(12) United States Patent
Fitzgerald

(10) Patent No.: US 7,608,416 B2
(45) Date of Patent: Oct. 27, 2009

(54) TARGETING MPGES-1 AS A TREATMENT FOR INFLAMMATION WHICH AVOIDS CARDIOVASCULAR RISK

(75) Inventor: Garret A. Fitzgerald, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 197 days.

(21) Appl. No.: 11/296,979

(22) Filed: Dec. 7, 2005

(65) Prior Publication Data

US 2006/0135490 A1     Jun. 22, 2006

Related U.S. Application Data

(60) Provisional application No. 60/633,777, filed on Dec. 7, 2004.

(51) Int. Cl.
C12Q 1/533 (2006.01)
G01N 33/53 (2006.01)
C12N 9/90 (2006.01)

(52) U.S. Cl. .............. 435/25; 435/7.1; 435/233

(58) Field of Classification Search ............ 435/25, 435/7.1, 233
See application file for complete search history.

(56) References Cited

U.S. PATENT DOCUMENTS

2003/0106085 A1*  6/2003  Audoly et al. ............... 800/18
2003/0171287 A1*  9/2003  Morishita et al. ............ 514/12
2004/0152148 A1*  8/2004  Lambalot ..................... 435/25

OTHER PUBLICATIONS

Henriksson et al., "In vivo production of prostacycline and thromboxane in patients with acute myocardial infarction," Br Heart J 55:543-548, 1985.*
Wübert et al., "Simultaneous solid phase extraction, derivitization, and gas chromatographic mass spectrometric quantification of thromboxane and prostacyclin metabolites, prostaglandins, and isoprostanes in urine," Anal Chem 69:2143-2146, 1987.*
FitzGerald et al., 2001, N. Engl. J. Med. 345: 433-442.
Dannhardt et al., 2001, Eur. J. Med. Chem. 36: 109-126.
Bombardier et al., 2000, N. Engl. J. Med. 343: 1520-8, 2 p following 8.
McAdam et al., 1999, Proc. Natl. Acad. Sci. USA 96: 272-7.
Catella-Lawson et al., 1999, J. Pharmacol. Exp. Ther. 289: 735-41.
Cheng et al., 2002, Science 296: 539-541.
Morishita et al., 1990, J. Clin. Invest. 86: 1885-91.
Dowd et al., 2001, J. Clin. Invest. 108: 585-90.
Thomas et al., 1998, J. Clin. Invest. 102: 1994-2001.
Qi et al., 2002, J. Clin. Invest. 110: 61-9.
Francois et al., 2004, Hypertension 43: 364-9.
Kobayashi et al., 2004, J. Clin. Invest. 114: 784-94.

(Continued)

*Primary Examiner*—Karen Cochrane Carlson
*Assistant Examiner*—Rosanne Kosson
(74) *Attorney, Agent, or Firm*—Drinker Biddle & Reath

(57) ABSTRACT

The present invention relates to methods for the treatment of inflammation and pain without increasing cardiovascular risk by administration of an inhibitor of mPGES-1. The invention further is related to identifying inhibitors of mPGES-1 that do not increase cardiovascular risk when administered to an individual.

8 Claims, 17 Drawing Sheets

OTHER PUBLICATIONS

Cayatte et al., 2000, Arterioscler. Thromb. Vasc. Biol. 20: 1724-8.
Huo et al., 2003, Nat. Med. 9: 61-7.
FitzGerald, 2004, N. Engl. J. Med. 351: 1709-11.
Jakobsson et al., 1999, Proc. Natl. Acad. Sci. USA 96: 7220-7225.
Pini et al., 2005, Arterioscler. Thromb. Vasc. Biol. 25: 315-20.
Schneider et al., 2004, Kidney International. 65: 1205-13.
Trebino et al., 2003, PNAS 100: 9044-9049.
Fahmi et al., 2004, Curr. Opin. Rheumatology 16: 623-627.
Kojima et al., 2005, Fundam. Clin. Pharmacol. 19: 255-261.
Fabre et al., 2001, J. Clin. Invet. 107: 603-610.
Pratico et al., 1995, J. Biol. Chem. 270: 9800-9808.
Pratico et al., 1998, Proc. Natl. Acad. Sci. USA 95: 3449-3454.
Lawson et al., 1999, J. Biol. Chem., 274(35): 24441-24444.
Masse et al., 2005, J. Biomol. Screen. 10: 599-605.
Percival, 2003, Anal. Biochem. 313: 307-310.
Paramo et al., 2005, Current Drug Targets—Cardiovascular & Hematological Disorders 5(4): 303-311(9).
Kamei et al., 2004, J. Biol. Chem. 279(32): 33684-95.
Thoren et al., 2000, Eur. J. Biochem. 267: 6428-6434.
Thoren et al., 2003, J. Biol. Chem. 278:22199-22209.
Ciabattoni et al., 1979, J. Endocrinol. Invest. 2:173-182.

* cited by examiner

TARGETING MPGES-1 AS A TREATMENT FOR INFLAMMATION WHICH AVOIDS CARDIOVASCULAR RISK

CROSS-REFERENCE TO RELATED APPLICATIONS

The present application is entitled to priority under 35 U.S.C. § 119(e), to U.S. Provisional Application No. 60/633,777, filed on Dec. 7, 2004, which application is hereby incorporated herein by reference in its entirety.

STATEMENT REGARDING FEDERALLY SPONSORED RESEARCH OR DEVELOPMENT

This invention was supported in part by funds obtained from the U.S. Government (National Institute of Health grant numbers HL-62250 and HL-70128), and the U.S. Government may therefore have certain rights in the invention.

BACKGROUND OF THE INVENTION

Prostaglandin synthase (PGHS) is the enzyme that mediates biosynthesis of prostaglandins (PGs) and thromboxane ($TxA_2$) from arachidonic acid, and whose inhibition underlies the effectiveness of a variety of anti-inflammatory drugs (Sharma and Sharma, 1997, Indian J. Exp. Biol. 35: 1025-1031; Morteau, 2000, Arch. Immunol. Ther. Exp. 48: 473-480; Llorens, 2002, J. Mol. Graph Model. 20: 359-371; Smith et al., 2000, Annu. Rev. Biochem. 69: 145-182; FitzGerald and Patrono, 2001, N. Engl. J. Med. 345: 433-442; Vane and Botting, 1998, Inflamm. Res. 47: S78-S87). PGHS activity originates from two distinct and independently regulated isozymes, PGHS-1 and PGHS-2 (Dannhardt and Kiefer, 2001, Eur. J. Med. Chem. 36: 109-126; Otto and Smith, 1995, J. Lipid Mediat. Cell. Signal. 12: 139-156; Oberle et al., 1998, Circ. Res. 82: 1016-1020). PGHS-2 is the dominant source of PGs which mediate pain and inflammation, while PGHS-1 catalyzes the formation of PGs that subserve housekeeping functions, such as the maintenance of gastrointestinal (GI) integrity. Traditional non-steroidal anti-inflammatory drugs (NSAIDs) inhibit both PGHS-1 and PGHS-2. A consequence of PGHS-1 inhibition, however, has been adverse gastrointestinal effects, including both direct and indirect irritation of the gastrointestinal tract, on NSAID therapies.

The coxibs, selective inhibitors of PGHS-2, were designed to inhibit the major enzymatic source of the PGs which mediate pain and inflammation, while sparing PGHS-1-derived PGs, which contribute dominantly to gastric cytoprotection (FitzGerald and Patrono, 2001, N. Engl. J. Med. 345: 433-42). Two coxibs, rofecoxib (Bombardier et al., 2000, N. Engl. J. Med. 343:1520-8, 2 p following 8) and lumiracoxib (Schnitzer et al., 2004, Lancet 364:665-74) have been shown in controlled trials to reduce the incidence of serious gastrointestinal (GI) adverse effects when compared with traditional NSAIDs.

All of the coxibs depress substantially the level of prostacyclin ($PGI_2$), leaving platelet COX-1-derived thromboxane $A_2$ ($TxA_2$) level unaffected (McAdam et al., 1999, Proc. Natl. Acad. Sci. USA 96: 272-7; Catella-Lawson et al., 1999, J. Pharmacol. Exp. Ther. 289; 735-41). $PGI_2$, the dominant product of arachidonic acid in macrovascular endothelial cells, is formed by prostacyclin synthase (PGIS) action on prostaglandin endoperoxide intermediates, which are produced catalytically by PGHS-2 (Moncada et al., 1976, Nature 263: 663-5). $PGI_2$ exhibits properties of potential relevance to atheroprotection. Specifically, it inhibits platelet aggregation, vascular smooth muscle contraction and proliferation (Cheng et al., 2002, Science 296: 539-541), leukocyte-endothelial cell interactions (Della Bella et al., 2001, Prostaglandins 65: 73-83) and cholesteryl ester hydrolase (Gryglewski et al., 1995, Ann. N.Y. Acad. Sci. 748: 194-206; discussion 206-7). It also activates reverse cholesterol transport (Morishita et al., 1990, J. Clin. Invest. 86: 1885-91). Indirect evidence suggests that $PGI_2$ protects against oxidant-induced tissue injury. Deletion of the $PGI_2$ receptor (IP) or suppression of $PGI_2$ biosynthesis augments cardiac injury caused by ischemia/reperfusion (Xiao et al., 2001, Circulation 104: 2210-5) or the anthracycline, doxarubacin (Dowd et al., 2001, J. Clin. Invest. 108: 585-90).

$PGI_2$ also limits the cardiovascular effects of thromboxane $A_2$ ($TxA_2$), the major PGHS-1 product of platelets (Cheng et al., 2002, Science 296: 539-541). The cardiovascular effects of $TxA_2$ include: platelet aggregation (Thomas et al., 1998, J. Clin. Invest. 102:1994-2001), elevation of blood pressure (Qi et al., 2002, J. Clin. Invest. 110: 61-9; Francois et al., 2004, Hypertension 43:364-9) and acceleration of atherogenesis (Kobayashi et al., 2004, J. Clin. Invest. 114:784-94; Cayatte et al., 2000, Arterioscler. Thromb. Vasc. Biol. 20: 1724-8; Huo et al., 2003, Nat. Med. 9: 61-7).

Rofecoxib has been associated with an excess of heart attack and stroke in patients receiving this drug (25 mg/day) in the Adenomatous Polyp Prevention on VIOXX® (APPROVe) trial, and has recently been withdrawn from the market (FitzGerald, 2004, N. Engl. J. Med. 351:1709-11). A similar excess in cardiovascular events has recently been reported with celecoxib, again in a trial designed to prevent colonic adenomas (www(dot)nih(dot)gov/news/pr/dec2004/od-17(dot)htm). Furthermore, evidence has emerged to link a structurally distinct coxib, valdecoxib, to a cardiovascular hazard (Ott et al., 2003, J. Thorac. Cardiovasc. Surg. 125: 1481-92), suggesting strongly that this increased cardiovascular risk is a class effect for the coxibs. Indeed, valdecoxib has also been recently withdrawn from the market (www(dot)fda(dot)gov/bbs/topics/news/2005//NEW01171 (dot)html).

Due to their undesirable side effects, alternatives to NSAIDs and coxibs are being sought for treatment of inflammation and pain. In this regard, attention has turned to microsomal prostaglandin E synthase-1 (mPGES-1), a stimulus-inducible enzyme that functions downstream of PGHS-2 in the production of prostaglandin $E_2$ ($PGE_2$) (see, e.g., Jakobsson et al., 1999, Proc. Natl. Acad. Sci. USA 96:7220-7225). mPGES-1 enzyme colocalizes with both PGHS enzymes (Pini et al., 2005, Arterioscler. Thromb. Vasc. Biol. 25:315-20; Schneider et al., 2004, Kidney Int. 65:1205-13). $PGE_2$ has been shown to be involved in arthritis and inflammation and thus, mPGES-1 has been suggested as a new drug target (see, e.g., Trebino et al., 2003, PNAS 100:9044-9049; Fahmi et al., 2004, Curr. Opin. Rheumatology 16:623-627; Kojima et al., 2005, Fundam. Clin. Pharmacol. 19:255-261).

To date, however, the cardiovascular profile of mPGES-1 and $PGE_2$ has not been determined. Specifically, it is unknown whether selective inhibition of $mPGE_2$ would avoid the undesirable cardiovascular consequences of PGHS-2 inhibtion. There is reason to think it might not. Suppression of $PGE_2$ is thought to account for the hypertension the can accompany treatment with NSAIDs or coxibs. In addition, $PGE_2$ affects platelet aggregation in variable, concentration dependent ways (Fabre et al., 2001, J. Clin. Invet. 107:603-610). In particular, at low concentration, $PGE_2$ enhances platelet aggregation, suggesting depressing $PGE_2$ levels by inhibitng mGPES-1 may have undesirable side effects, such as accelerating thrombogenesis.

There exists a need in the art for a treatment for inflammation and pain that does not cause an elevated cardiovascular risk. The present invention addresses and meets these needs.

SUMMARY OF THE INVENTION

In one aspect of the invention, a method of treating inflammation in an individual is provided, the method comprising the steps of administering a therapeutically effective amount of an inhibitor of microsomal prostaglandin E2 synthase (mPGES-1) to the individual, wherein the inhibitor does not increase the risk of a cardiovascular event in the individual.

In one embodiment, administration of the inhibitor does not reduce the level of prostacyclin in the individual when compared to the level of prostacyclin in the individual in the absence of the administration of the inhibitor.

In another embodiment, administration of the inhibitor increases the level of prostacylin in the individual when compared to the level of prostacyclin in the individual in the absence of the administration of the inhibitor.

In yet another embodiment, administration of the inhibitor does not alter the level of thromboxane in the individual when compared to the level of thromboxane in the individual in the absence of the administration of the inhibitor.

In one embodiment, the cardiovascular event is selected from the group consisting of deep vein thrombosis, pulmonary thrombosis, atherogenesis, atherosclerosis, myocardial infarction, cardiac arrest, stroke, angina, and congestive heart failure.

In another aspect of the invention, a method of identifying an inhibitor of mPGES-1 that does not increase risk of a cardiovascular event in an individual is provided, the method comprising the steps of measuring a first level of prostacyclin and a first level of $PGE_2$ produced by a cell that expresses mPGES-1, administering a test compound to the cell, measuring a second level of prostacylin and a second level of $PGE_2$ produced by the cell, wherein a test compound that reduces the second level of $PGE_2$ compared to the first level of $PGE_2$ and that does not decrease the second level of prostacyclin compared to the first level of prostacyclin is identified as an inhibitor of mPGES-1 that does not increase risk of a cardiovascular event in an individual when administered to the individual.

In one embodiment, the second level of prostacylin is about the same as the first level of prostacyclin. In another embodiment, the second level of prostacyclin is greater than the first level of prostacyclin.

In one embodiment, the cell is an endothelial cell. In another embodiment, the endothelial cell is a murine endothelial cell or a human endothelial cell. In yet another embodiment, the murine endothelial cell comprises a human mPGES-1 gene.

In one embodiment, the cell is part of an organism. In another embodiment, the first and second levels of $PGE_2$ and prostacyclin are measured in urine samples obtained from the organism. In one embodiment, the organism is a mouse and in another embodiment, the mouse expresses human mPGES-1.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
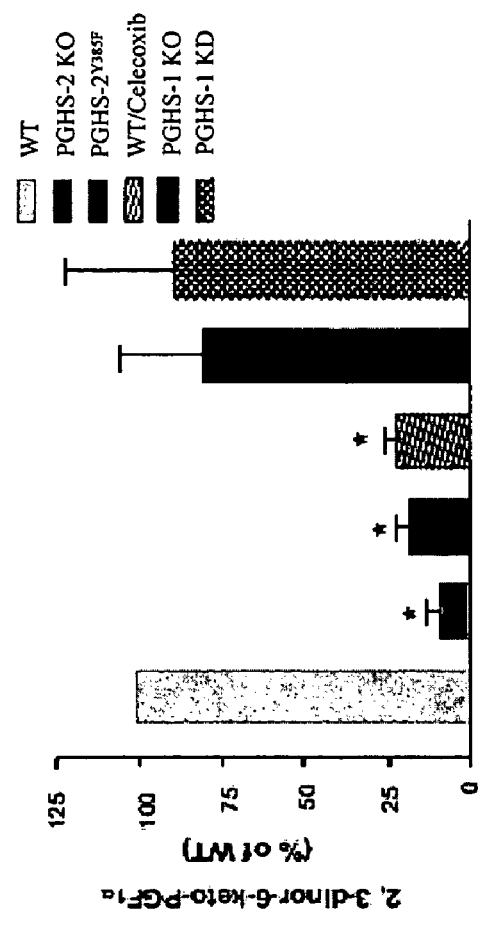
FIG. 1 is a series of graphs depicting the amount of two urinary prostaglandin metabolites, PGIM and TxM, as a function of PGHS-1 and PGHS-2 activity. (* P<0.001)
Figure 1:
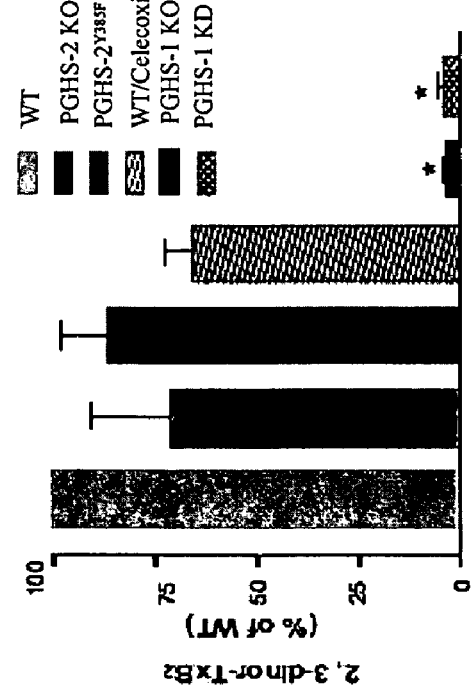

The invention arises from the observation disclosed herein that mPGES-1 is a major source of $PGE_2$ and further, that mPGES-1 deletion is as effective as traditional NSAIDs in treating pain and inflammation in art-recognized animal models. Although suppression of $PGE_2$, perhaps even more than prostacyclin ($PGI_2$), is thought to account for hypertension on NSAIDs, including those selective for PGHS-2, remarkably, thrombogenesis is not accelerated in mPGES-1$^{-/-}$ mice. As demonstrated for the first time herein, deletion of mPGES-1 augments $PGI_2$ biosynthesis in vivo, likely by diversion of the $PGH_2$ substrate to PGI synthase, without a significant alteration in formation of thromboxane ($TxA_2$). While not wishing to be bound by theory, given that prostacyclin receptor (IP) deletion results in hypertension and an exaggerated hypertensive response to dietary salt, it is believed that increased $PGI_2$ may offset the hypertensive consequence of suppressing $PGE_2$. Most notably, deletion of mPGES-1 delays atherogenesis.

Consequently, the present application features a method of treating inflammation or pain without increasing cardiovascular risk. The method comprises administering an inhibitor of mPGES-1 to an individual in need thereof. The invention further features methods for identifying inhibitors of mPGES-1 that do not increase cardiovascular risk.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for the synthesis and manipulation of nucleic acid and peptides. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y.; Ausubel et al., 2002, Current Protocols in Molecular Biology, John Wiley & Sons, New York, N.Y.; Gerhardt et al. eds., 1994, Methods for General and Molecular Bacteriology, American Society for Microbiology, Washington, D.C.), which are provided throughout this document.

The articles "a" and "an" are used herein to refer to one or to more than one (i.e., to at least one) of the grammatical object of the article. By way of example, "an element" means one element or more than one element.

As used herein, "treating inflammation and/or pain" means reducing the frequency with which inflammation and/or pain is experienced by a patient. "Treating inflammation and/or pain" also encompasses alleviating inflammation and/or pain, which means the severity of the symptom is reduced.

"PGHS" is used herein to refer to an enzyme (EC 1.14.99.1) having both peroxidase and cyclooxygenase activity. These enzymes catalyze the formation of prostaglandins and thromboxane from arachidonic acid by means of these activities. Alternative names include: fatty acid cyclooxygenase, prostaglandin-endoperoxide synthase, prostaglandin-endoperoxide synthetase, prostaglandin synthase, prostaglandin synthetase, PG synthetase, (PG)H synthase, and prostaglandin G/H synthase. There are two isoforms of PGHS, referred to as PGHS-1 and PGHS-2. Alternative names for these enzymes include COX-1 and COX-2, respectively.

A "non-steroidal anti-inflammatory drug" (NSAID) is used herein to refer to a drug which has analgesic, antipyretic and anti-inflammatory effects. Traditional NSAIDs are non-selective inhibitors of both PGHS-1 and PGHS-2. Examples of non-selective NSAID inhibitors include: aspirin, ibuprofen, naproxen, indomethacin, and meclofenamic acid. While acetaminophen (paracetamol) is sometimes listed as an NSAID, due to its inhibitory actions on cyclooxygenase, it lacks significant anti-inflammatory properties and is, therefore, not considered to be a true NSAID.

As used herein, "PGHS-2 selective inhibitor compound", "PGHS-2 selective inhibitor" or "coxib" refers to a compound which inhibits PGHS-2 to a greater extent than it inhibits PGHS-1. Some non-limiting examples of PGHS-2 selective inhibitor compounds include: nimesulide, meloxicam, diclofenac, parecoxib (Dynastat®), celecoxib (Celebrex®), etoricoxib (Arcoxia®), lumiracoxib (Prexige®), rofecoxib (Vioxx®), and valdecoxib (Bextra®). A PGHS-2 selective inhibitor compound generally has a selectivity ratio of cyclooxygenase-2 inhibition over cyclooxygenase-1 inhibition of at least about 5, more preferably about 10, and more preferably about 50. Inhibition is preferably assessed using a whole blood assay (FitzGerald and Patrono, 2001, N. Engl. J. Med. 345:433-442).

As used herein, "mPGES-1" refers to microsomal prostaglandin E synthase (EC 5.3.99.3), isoform 1. Alternative names and abbreviations used in the art for this enzyme include microsomal glutathione S-transferase 1-like 1 (MGST1-L1), prostaglandin-$H_2$ E-isomerase and PTGES1. This enzyme catalyzes the isomerization of $PGH_2$ into $PGE_2$.

As used herein, "mPGES-1 inhibitor compound" or "mPGES-1 inhibitor" refers to a compound which inhibits mPGES-1 enzymatic activity thereby reducing $PGE_2$ biosynthesis. Some non-limiting examples of PGHS-2 inhibitor compounds include: sulindac sulfide, dexamethasone, arachidonic acid, NS-398, leukotriene C4, 15-deoxy-delta (12,14)-prostaglandin J(2) (15-d-PGJ2) and omega-3 fatty acids, such as docosahexaenoic acid and eicosapentaenoic acid.

As used herein, mPGES-1 inhibitor compound or mPGES-1 inhibitor that "does not increase cardiovascular risk" is one that does not significantly decrease the level of prostacyclin when it is administered. Preferably, it increases the level of prostacylin. More preferably still, it delays or prevents atherogenesis.

"Increased cardiovascular risk" is used herein to refer to an increase in the likelihood or possibility of incurring or experiencing a cardiovascular event. With regard to cardiovascular risk and a medicament, the risk can be assessed relative to a patient's own risk when not taking the medicament, or with respect to a population that does not have clinical evidence of a cardiovascular disease and/or is not at risk for a cardiovascular event and is not taking the medicament. The population may be representative of the patient with regard to approximate age, age group and/or gender.

"Cardiovascular event" as used herein refers to a disorder or disease of the cardiovascular system having a sudden onset; it can also refer to a sudden worsening of such a disorder or disease. Examples of cardiovascular events include, without limitation: cardiac arrest, myocardial infarction, thrombosis, deep vein thrombosis, pulmonary thrombosis, atherogenesis, atherosclerosis, plaque fracture, ischemia, stroke, worsening of angina, and congestive heart failure.

As used herein, "sudden" refers to a short period time encompassing a few minutes to several hours or several days.

"Clinical evidence of cardiovascular disease" is used herein to refer to medical evidence indicative of cardiovascular disease, as established by American College of Cardiology guidelines current at the time of filing of this application. Such clinical evidence includes, but is not limited to, abnormal results from: blood pressure, blood tests including a lipid profile, high density cholesterol, low density, cholesterol, triglycerides, cardiac biomarkers (enzymes, proteins, and hormones, such as troponin, myoglobin, b-type natriuretic peptide and creatine phosphokinase, that are associated with heart function, damage or failure), electrocardiograms (ECG or EKG), stress tests, chest x-ray, MUGA scan, computed tomography (CT), nuclear scanning (nuclear heart scan), echocardiogram (heart ultrasound), cardiac catheterization (coronary angiography), duplex/doppler ultrasound, magnetic resonance angiography (MRA) and magnetic resonance imaging (MRI). Documented incidents of myocardial infarctions, heart attack or plaque-associated thrombus are also clinical evidence of cardiovascular disease.

"Genetic predisposition for elevated cardiovascular risk" as used herein refers to having at least one genetic mutation that is correlated with increased risk of a cardiovascular event. Such genetic predispositions include, but are not limited to: familiar hypercholesterolemia and hypercoagulable disorders including Factor V Leiden, prothrombin gene mutation, antithrombin III deficiency, protein C deficiency, protein S deficiency and homocystinuria.

"$PGE_2$" as used herein refers to prostaglandin $E_2$.

"$PGE_2$ metabolite" as used herein regers to a byproduct of $PGE_2$ metabolism in an animal, preferably in a mammal. As used herein, "PGEM" refers to the $PGE_2$ metabolite 9,15-dioxo-11α-hydroxy-2,3,4,5-tetranor-prostan-1,20-dioic-17,17,18,18,19,19-$d_6$ acid.

"$TxA_2$" as used herein to refer to thromboxane.

"Thromboxane metabolite" as used herein refers to a byproduct of thromboxane metabolism in an animal, preferably in a mammal. Non-limiting examples of thromboxane metabolites include: 2,3-dinor thromboxane $B_2$ (2,3-dinor-$TxB_2$), 11-dehydro-thromboxane $B_2$ (11-dehydro $TxB_2$), 2,3,4,5-tetranor-thromboxane $B_1$ and 2,3-dinor-thromboxane $B_1$. 11-Dehydro $TxB_2$ is the most abundant thromboxane metabolite in human urine. As used herein, "TxM" refers to the thromboxane metabolite 2,3-dinor-$TxB_2$.

"$PGI_2$" is used herein to refer to prostacyclin, also known as epoprostenol.

"$PGI_2$ metabolite" as used herein refers to a byproduct of prostacyclin metabolism in an animal, preferably in a mammal. Non-limiting examples of $PGI_2$ metabolites are 2,3-dinor-6-keto $PGF_{1\alpha}$ and 15-keto-13,14-dihydro-2,3-dinor-6-keto-$PGF_{1\alpha}$. The most abundant $PGI_2$ metabolite in human urine is 2,3-dinor-6-keto $PGF_{1\alpha}$. As used herein, "PGIM" refers to the prostacyclin metabolite 2,3-dinor-6-keto-$PGF_{1\alpha}$.

"Isoprostane" as used herein refers to a free-radical-catalyzed prostaglandin isomer formed from arachidonic acid. An isoprostane is an isomer of a prostaglandin. Non-limiting examples include: $iPF_{2\alpha}$-III (also known as 8-iso-$PGF_{2\alpha}$; 8-epi-$PGF_{2\alpha}$; $IPF_{2\alpha}$-IV; and 15-$F_{2t}$-IsoP), $IPF_{2\alpha}$-IV (also known $IPF_{2\alpha}$-III), $IPF_{2\alpha}$-V (also known $IPF_{2\alpha}$-II), $IPF_{2\alpha}$-VI (also known as 5-$F_{2t}$-IsoP and $IPF_{2\alpha}$-I), and 8,12-iso-$IPF_{2\alpha}$-VI (also known as 8,12-iso-$IPF_{2\alpha}$-I and 5-$F_{2c}$-IsoP).

As used herein, "therapeutically effective amount" refers to a nontoxic but sufficient amount of an agent to provide the desired biological result. That result can be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

DESCRIPTION OF THE INVENTION

Methods for Treatment of Inflammation and/or Pain

The present application features methods for treating inflammation or pain without increasing cardiovascular risk. The method comprises administering a therapeutically effective amount of an inhibitor of mPGES-1 to an individual in need thereof.

Individuals for whom the method is useful include any animals that express mPGES-1. Non-limiting examples of such animals are mammals, such as humans, non-human primates, cattle, horses, dogs, sheep, goats, mice, rats and pigs. Preferably, the individual is a human. Treatment according to the methods of the invention may be particularly useful for individuals with clinical evidence of cardiovascular risk or a genetic predisposition for elevated cardiovascular risk.

The methods for alleviating inflammation and/or pain are useful for any condition characterized wholly or in part by symptoms of pain and/or inflammation. Conditions may be chronic or acute. Non-limiting examples of conditions suitable for treatment using the methods of the invention include:

osteoarthritis, primary dysmenorrheal, secondary dysmenorrheal, headaches, including sinus headaches and migraines, post-surgical pain and/or inflammation, rheumatoid arthritis, tendonitis, bursitis, gouty arthritis, polymyalgia rheumatica, fibermyalgia, neuropathy, systemic lupus erythematosus, soft tissue injury, myalgia, neuralgia, neuritis, nociceptive pain, neuropathic pain, muscoskeletal pain, and inflammation and pain associated with bacterial or viral illnesses, such as influenza, the common cold, or periodontal disease.

mPGES-1 inhibitors include, but are not limited to, sulindac sulfide, dexamethasone, arachidonic acid, NS-398, leukotriene C4, 15-deoxy-delta(12,14)-prostaglandin J(2) (15-d-PGJ2), omega-3 fatty acids, such as docosahexaenoic acid and eicosapentaenoic acid, and all other known and unknown inhibitors. Preferably, the mPGES-1 inhibitor is selective for inhibition of mPGES-1. Selective mPGES-1 inhibitors are those which inhibit mPGES-1 to a greater extent than other enzymes, such as, but not limited to, PGHS-2 and PGHS-1. Preferably, the selective mPGES-1 inhibitor inhibits mPGES-1 to a greater extent than it inhibits PGHS-2. Preferably a mPGES-1 inhibitor has a selectivity ratio of mPGES-1 inhibition over PGHS-2 inhibition of at least about 5, more preferably about 10, and more preferably about 50.

Administration of mPGES-1 Inhibitors

The therapeutic methods of the invention encompass the use of pharmaceutical compositions of an appropriate small molecule, protein or peptide and/or isolated nucleic acid that inhibits mPGES-1 to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 μM and 10 μM in a mammal.

Typically dosages of an mPGES-1 inhibitor which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include, but are not limited to, aspirin, a thromboxane receptor antagonist, an ADP receptor antagonist, such as clopidogrel, a statin and a vitamin preparation Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Identifying Inhibitors of mPGES-1

The instant invention also features methods for identifying an inhibitor of mPGES-1 that does not increase risk of a cardiovascular event.

Inhibitors of mPGES-1 activity may be identified by screening test compounds. For instance, inhibitors of mPGES-1 activity can be identified by screening test compounds in vitro, using mPGES-1 protein and assaying enzymatic activity in thre presence of a test compound and comparing it to enzymatic activity in the absence of the test compound. A test compound that reduces $PGE_2$ production by mPGES-1 is identified as an mPGES-1 inhibitor. Enzymatic activity may be screened by assaying, directly or indirectly, the amount of $PGE_2$ produced by mPGES-1, using any method known to the skilled artisan and as described elsewhere herein.

Alternatively, inhibitors of mPGES-1 activity may be identified by screening test compounds in vitro using cells that express an mPGES-1 gene. Nonlimiting examples of such cells include endothelial cells, particular vascular endothelial cells, smooth muscle cells, synovial cells and macrophages. Expression of mPGES-1 may be from an endogenous mPGES-1 gene. Alternatively, the mPGES-1 may be expressed from a heterologous gene introduced into the cell by recombinant methods. The introduced heterologous nucleic acid may be present transiently, or may be present stably in the cell, for instance due to insertion into the cell's chromosomal material. Expression of the endogenous or heterologous gene may be constitutive or inducible. For instance, the endogenous mPGES-1 promoter may be stimulated by exposure to lipopolysaccharide.

The skilled artisan is familiar with the many methods of introducing heterologous nucleic acid into a cell, as well as the sequence elements necessary for transcription and translation of a coding sequence. See, for instance, Sambrook et al. (2001, Molecular Cloning: A Laboratory Manual, Cold Spring Harbor Laboratory Press, Cold Spring Harbor, N.Y.), in Ausubel et al. (eds., 1997, Current Protocols in Molecular Biology, John Wiley & Sons, New York), and in Gerhardt et al. (eds., 1994, Methods for General and Molecular Bacteriology, American Society for Microbiology, Washington, D.C.). In a preferred embodiment of the method for identifying inhibitors of mPGES-1, the mPGES-1 coding sequence, or variant thereof, is from the same organism that is the intended recipient of treatment with the so-identified mPGES-1 inhibitor.

mPGES-1 coding sequences have been obtained and sequenced in several organisms, and any one can be used in the instant invention. mPGES-1 coding sequences useful in the instant invention include, but are not limited to: human mPGES-1 (mRNA, NCBI GenBank® Accession number NM_004878, SEQ ID NO. 1; protein, SEQ ID NO. 2), mouse mPGES (mRNA, NCBI GenBank® Accession number NM_022415, SEQ ID NO. 3; protein, SEQ ID NO. 4), rat mPGES mRNA, (NCBI GenBank® Accession number NM_021583, SEQ ID NO. 5; protein, SEQ ID NO. 6), bovine (mRNA, NCBI GenBank® Accession number AY032727, SEQ ID NO. 7; protein, SEQ ID NO. 8), horse (mRNA NCBI GenBank® Accession number AY057096, SEQ ID NO. 9; protein, SEQ ID NO. 10) and zebrafish (mRNA NCBI GenBank® Accession number AY724691, SEQ ID NO. 11; protein, SEQ ID NO. 12). Procine mPGES-1 has recently been cloned as well (NCBI GenBank® Accession number AY857634, Waclawik et al., 2005, Endocrinology 2005 Oct. 13; [Epub ahead of print]). Furthermore, any sequence encoding a variant mPGES-1 protein can be used, provided the mPGES-1 variant protein retains the activity of producing $PGE_2$. Methods for assessing $PGE_2$ production are discussed elsewhere herein.

The heterologous mPGES-1 coding sequence may be operably linked to other nucleic acid sequences. Nonlimiting examples of other nucleic acid sequences are inducible promoters and other coding sequences, such as protein tags. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Inducible promoters are useful for controlled overexpression of the mPGES-1 coding sequence. The inducible promoter may be that normally linked to the mPGES-1 coding sequence or may be from another gene. Protein tags, such as affinity tags or epitopes, are useful, for instance, in simplifying purification of the fusion protein. Sequences of inducible promoters and protein tags are well known in the art to the skilled artisan.

To identify a test compound as an inhibitor of mPGES-1, $PGE_2$ production in the cell is assessed in the presence of the test compound and compared to $PGE_2$ production in the cell in the absence of the test compound. A test compound that reduces $PGE_2$ production by mPGES-1 is identified as an mPGES-1 inhibitor. The skilled artisan is knowledgeable about the appropriate control experiments necessary to confirm that an inhibitor is acting directly on mPGES-1. Enzymatic activity may be screened by assaying directly or indirectly the amount of $PGE_2$ produced in a cell, using any method known to the skilled artisan. Exemplary methods are described elsewhere herein.

Inhibitors of mPGES-1 activity can also be identified by screening test compounds using organisms, such as mice, that express mPGES-1. The organism may express an endogenous mPGES-1 or a heterologous mPGES-1. In one embodiment, expression of the endogenous mPGES-1 gene is reduced or eliminated by standard known to the skilled artisan, including but not limited to gene knock out, gene knock down and RNAi, and a heterologous mPGES-1 gene is introduced into a cell in the organism. The organism may be a transgenic animal.

$PGE_2$ level may be assessed directly or indirectly in biological samples from the organism after exposure to a test compound, and compared to $PGE_2$ level in the absence of the test compound. A test compound that reduces $PGE_2$ production by mPGES-1 is identified as mPGES-1 inhibitor. The skilled artisan is knowledgeable about the appropriate control experiments necessary to confirm that an inhibitor is acting directly on mPGES-1. Suitable biological samples for detection of $PGE_2$ directly or indirectly include, but are not limited to, tissues, blood (whole blood or plasma) and urine. In one embodiment, $PGE_2$ levels are assessed indirectly by measuring the level of a $PGE_2$ metabolite in a biological sample. In one aspect, the $PGE_2$ metabolite is PGEM. In another aspect, the biological sample is urine and the $PGE_2$ metabolite measured is PGEM.

Advantageously, assaying test compounds for their capacity to inhibit mPGES-1 in a cell or an organism enables biomarkers of cardiovascular risk to be measured as well. There are numerous cardiovascular risk markers that may be monitored, including blood components associated with cardiovascular risk, that may be measured in an organism. Blood component parameters that are correlated with cardiovascular risk include, but are not limited to: total cholesterol, LDL cholesterol, homocysteine, triglycerides, C-reactive protein (CRP), monocyte chemoattractant protein-1 (MCP-1) and certain cytokines. Cytokines correlated with cardiovascular risk include, but are not limited to, soluble intracellular adhesion molecule-1 (sICAM-1), interleukin-6 (IL-6) and tumor necrosis factor-α (TNFα). Preferably, cardiovascular risk is assessed by measuring changes in the levels of isoprostanes and/or prostanoids in the presence and absence of the test compound. Advantagously, prostanoids may be measured in either cell culture or in biological samples from an organism. Exemplary methods for cardiovascular risk assessment are disclosed in U.S. patent application Ser. No. 11/210,378, filed Aug. 24, 2005. In particular, the levels of $8,12$-iso-$iPF_{2\alpha}$-VI, $PGI_2$ and/or $TxA_2$ may be measured in the presence and absence of a test compound, in addition to $PGE_2$. An inhibitor of mPGES-1 that does not increase cardiovascular risk is one that does not depress levels of $PGI_2$ or increase levels of $TxA_2$ or of $8,12$-iso-$iPF_{2\alpha}$-VI. In a preferred embodiment, an inhibitor of mPGES-1 increases the level of $PGI_2$.

Test compounds identified as mPGES-1 inhibitors using purified mPGES-1 enzyme may subsequently be tested in a cell that expresses one or both of PGHS-1 and PGHS-2, or in an organism to ascertain their effect on $PGI_2$ and $TxA_2$ levels, or another biomarker of cardiovascular risk. Alternatively, test compounds identified as mPGES-1 inhibitors may be tested using purified PGHS-1 and PGHS-2 enzymes.

Test compounds for use in the screening methods can be small molecules, nucleic acids, peptides, peptidomimetics and other drugs. The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors of mPGES-1 activity identified by the inventive method may be useful directly in therapeutic applications, and may also serve as lead drugs in the development of further therapeutics.

The level of $PGE_2$ produced by mPGES-1, in vitro or in vivo, can be assessed, directly or indirectly, using any method known to the skilled artisan for isolating and quantitating a prostaglandin molecule and are described herein by way of example. Such methods are described, for example, in Pratico et al., 1995, J. Biol. Chem. 270:9800-9808, Pratico et al., 1998, Proc. Natl. Acad. Sci. USA 95:3449-3454 and Lawson et al. (1999, J. Biol. Chem., 374(35) 24441-24444). These methods include, by way of example, and not by limitation, solvent extractions, solid phase extractions, centrifugation and sedimentation methods, quantitative and semi-quantitative methods such as chromatographic methods including thin layer chromatography, low, medium, and high pressure liquid chromatography methods, mass spectrometry methods, gas chromatography methods, gas chromatography/mass spectrometry methods, and immunological methods. Direct measurement can use a labeled substrate, for instance tritiated $PGH_2$, to yield readily-detected $PGE_2$. Masse et al. (2005, M. Biomol. Screen. 10:599-605) disclose a method of measuring PGE2 by EIA. Other immunological assays are well known in the art. See, e.g., Harlow et al., 1988, Antibodies: A Laboratory Manual, Cold Spring Harbor Laboratory Press, Cold Spring Harbor, N.Y. and Harlow et al., 1999, Using Antibodies: A Laboratory Manual, Cold Spring Harbor Laboratory Press, Cold Spring Harbor, N.Y. Indirect methods to assess $PGE_2$ includes that taught by Percival (2003, Anal. Biochem. 313:307-310), who discloses a method of coupling $PGE_2$ production to the formation of NADH, thereby permitting spectrophotometric detection.

An exemplary method for isolating $PGE_2$ from a biological sample comprises first obtaining a sample of a tissue or body fluid from an organism. Briefly, $PGE_2$ or a $PGE_2$ metabolite is isolated by first, in the case of a tissue sample, homogenizing the tissue sample. In the case of a body fluid sample, no homogenization step is necessary. Total lipids are then extracted from the sample using ice-cold Folch solution, chloroform/methanol (2:1,v/v). The solution is then centrifuged briefly, and the organic phase, which contains the extracted lipids, is dried under nitrogen. Lipids are then hydrolyzed using aqueous potassium hydroxide to release $PGE_2$ or the $PGE_2$ metabolite.

The $PGE_2$ or the $PGE_2$ metabolite isolated as described above is then measured using an assay method for a prostaglandin. Preferably, the assay is a quantitative assay. The level of $PGE_2$ or the $PGE_2$ metabolite is quantified based on the assay results using, for example, peak area or peak height ratios. An example of a preferred quantitative assay for a $PGE_2$ metabolite is described herein in the Examples.

For example, the $PGE_2$ or the $PGE_2$ metabolite isolated as described above can be measured as follows. Briefly, after potassium hydroxide hydrolysis, the sample which contains $PGE_2$ or the $PGE_2$ metabolite is spiked with a known amount of a synthetic homologous internal standard. A non-limiting example of an internal standard includes a radio-labeled synthetic homologous $PGE_2$ metabolite. The samples are then subjected to solid phase extraction, derivatized, and purified using thin layer chromatography. After thin layer chromatography, each sample is analyzed for $PGE_2$ or the $PGE_2$ metabolite content using gas chromatography-mass spectrometry, and quantitation is performed using peak area or peak height ratios of the radio-labeled synthetic homologous internal standard molecule and the $PGE_2$ or the $PGE_2$ metabolite molecule of interest.

Measurements made using a tissue sample can be made using any tissue sample obtained from any type of tissue. Measurements made using a sample of body fluid can be made in any type of body fluid. Preferably the body fluid sample is a sample obtained from the group consisting of plasma and urine. Most preferably, the body fluid sample is urine.

Urine is collected in sterile containers, preferably 30 minutes after voiding. Alternatively, urine is collected as a time integrated sample. For instance, after voiding, urine is collected for a time period, for instance 2, 4 or 6 hours. If the urine sample is not analyzed immediately, the sample is stored in such a way as to prevent or reduce breakdown of the component(s) to be measured in the urine. One method of storage to prevent or reduce breakdown is to freeze the sample on dry ice immediately after collection and store the frozen sample at −70° C.

Marker levels in urine are generally normalized to another urine component. Typically, the other urine component is creatinine. Creatinine is measured is preferably measured using an automated colorimetric assay (Sigma-Aldrich Co., St Louis, Mo.).

Other Methods

As demonstrated herein, reducing $PGE_2$ provides a therapeutic benefit in the treatment of inflammation and/or pain. The extent of reduction of $PGE_2$ in an individual on an mPGES-1 inhibition therapy is expected to directly correlate with the expected therapeutic benefit. That is, the greater the reduction in $PGE_2$ in the individual administered a mPGES-1 inhibitor, the greater the expected therapeutic benefit for the individual.

The levels of prostacyclin and thromboxane reflect the cardiovascular risk. In an individual on mPGES-1 inhibition therapy, the therapy is generally cardiovascularly neutral if neither the prostacyclin level nor the thromboxane level is changed compared to the levels in the absence of the mPGES-1 inhibitor. It is cardiovascularly favorable if the prostacylin level increases on mPGES-1 inhibition therapy. Likewise, it is cardiovascularly favorable if the thromboxane level decreases.

Assessing these biomarkers in an individual on or contemplating mPGES-1 inhibition therapy will provide numerous useful applications. The best scenario for balancing likely therapeutic benefit and minimized cardiovascular risk for an individual is that when an mPGES-1 inhibitor is administered to the individual, there is a reduction of $PGE_2$, there is no change or an increase in prostacylin and there is no change or a decrease in thromboxane compared to levels of each in the individual when not administered the inhibitor. Accordingly, a method of identifying a candidate for mPGES-1 therapy includes monitoring the level of these biomarkers in an individual. As used herein, a "candidate for mPGES-1 therapy" is one for whom a therapeutic benefit is expected without an increase in cardiovascular risk. For instance, such a method comprises measuring a first level of a $PGE_2$ metabolite and a first level of a prostacyclin metabolite in a biological sample obtained from the individual prior to initiating mPGES-1 inhibition therapy, measuring a second level of the $PGE_2$ metabolite and a second level of the prostacyclin metabolite in a biological sample obtained from the individual after initiating mPGES-1 inhibition therapy, wherein when the second level of the $PGE_2$ metabolite is reduced compared to the first level of the $PGE_2$ metabolite and wherein the second level of the prostacylin metabolite is not reduced compared to the first level of the prostacyclin metabolite, the individual is identified as being a candidate for mPGES-1 inhibition therapy. If the second level of prostacylin is increased compared to the first, the individual is also identified as a candidate. In one embodiment, the method further comprises measuring a second level of the thromboxane metabolite in a biological sample obtained from the individual after initiating mPGES-1 inhibition therapy, wherein when the second level of the thromboxane metabolite is not increased compared to the first level of the thromboxane metabolite, the individual is identified as being a candidate for mPGES-1 inhibition therapy.

Based on the disclosure herein, the skilled artisan can individualize mPGES-1 inhibition therapy for an individual by assessing the effects of a particular dosing regimen in order to optimize the balance of therapeutic benefit and cardiovascular risk. Accordingly, a method for assessing a dosage of mPGES-1 inhibitor in an individual undergoing mPGES-1 inhibition therapy for therapeutic benefit and cardiovascular risk includes measuring a first level of a PGE2 metabolite and a first level of a prostacyclin metabolite in a biological sample obtained from the individual prior to administering the dosage of mPGES-1 inhibitor, measuring a second level of the PGE2 metabolite and a second level of the prostacyclin metabolite in a biological sample obtained from the individual after administering the dosage of mPGES-1 inhibitor, wherein when the second level of the PGE2 metabolite is reduced compared to the first level of the $PGE_2$ metabolite and wherein the second level of the prostacylin metabolite is not reduced compared to the first level of the prostacylin metabolite, the dosage is identified as likely providing therapeutic benefit without increasing cardiovascular risk in that individual. If the second level of prostacylin is increased compared to the first, the dosage is identified as likely providing therapeutic benefit without increasing cardiovascular risk in that individual. In one embodiment, the method further comprises measuring a second level of the thromboxane metabolite in a biological sample obtained from the individual after initiating mPGES-1 inhibition therapy, wherein when the second level of the thromboxane metabolite is not increased compared to the first level of the thromboxane metabolite, the dosage is identified as likely providing therapeutic benefit without increasing cardiovascular risk in that individual. Such methods will allow the skilled practitioner to titrate the dose for a particular individual considering both the therapeutic benefit as well as minimizing the cardiovascular risk associated with the dose. Such methods also predict the likely extent of therapeutic benefit at a particular dosage because, as previously explained, the greater the reduction in $PGE_2$ in the individual administered an mPGES-1 inhibitor, the greater the expected therapeutic benefit for that individual.

A method of monitoring the therapeutic benefit and cardiovascular risk over time by assessing these biomarkers is also provided. The method comprises measuring a first level of a $PGE_2$ metabolite and a first level of a prostacyclin metabolite in a biological sample obtained from the individual prior to initiating mPGES-1 inhibition therapy in the indivdual, and measuring a second level of the $PGE_2$ metabolite and a second level of the prostacyclin metabolite in a biological sample obtained from the individual after initiating mPGES-1 inhibition therapy in the individual, wherein when the second level of the $PGE_2$ metabolite is reduced compared to the first level of the $PGE_2$ metabolite and wherein the second level of the prostacylin metabolite is not reduced compared to the first level of the prostacylin metabolite, the mPGES-1 inhibition therapy is considered to provide therapeutic benefit and does not increase risk of a cardiovascular event in the individual. Furthermore, when the second level of the prostacylin metabolite is increased compared to the first level of the prostacylin metabolite, the mPGES-1 inhibition therapy is considered to provide therapeutic benefit and does not increase risk of a cardiovascular event in the individual. In one embodiment, the method further includes measuring a first level of a thromboxane metabolite in a biological sample obtained from the individual prior to initiating mPGES-1 inhibition therapy, measuring a second level of the thromboxane metabolite in a biological sample obtained from the individual after initiating mPGES-1 inhibition therapy, wherein when the second level of the thromboxane metabolite is not increased compared to the first level of the thromboxane metabolite, the mPGES-1 inhibition therapy is considered to provide therapeutic benefit and does not increase risk of a cardiovascular event in the individual. On-going monitoring of an individual on a mPGES-1 inhibition therapy is expected to permit early detection of a decreased therapeutic effect and/or an increasing cardiovascular risk while on the therapy. Consequently, early intervention to adjust dosage or frequency of administration to improve therapeutic effect or reduce cardiovascular risk is possible.

For all of these contemplated methods, the preferred individual is a mammal, more preferably a human. The preferred biological sample is a urine sample. Urine samples may be obtained non-invasively and are readily processed for measuring biomarker and thus are the preferred biological sample. The preferred $PGE_2$ metabolite is 9,15-dioxo-11α-hydroxy-2,3,4,5-tetranor-prostan-1,20-dioic-17,17,18,18, 19,19-$d_6$ acid. The preferred prostacylin metabolite is 2,3-dinor-6-keto $PGF_{1\alpha}$. The preferred thromboxane metabolite is 11-dehydro $TxB_2$.

Kits

A kit is envisaged for every method disclosed herein. The following description of a kit useful for assessing likely therapeutic benefit in a mammal by measuring a $PGE_2$ metabolite in urine therefore is not intended to be limiting and should not be construed that way.

The kit comprises a negative control solution containing a $PGE_2$ metabolite at a concentration of about the concentration of the $PGE_2$ metabolite which is present in a tissue or body fluid sample of a mammal which is not undergoing mPGES-1 inhibition therapy. The kit also includes a positive control solution containing a $PGE_2$ metabolite at a concentration of about the concentration of the prostanoid metabolite which is present in a tissue or body fluid sample of a mammal which is at increased undergoin mPGES-1 inhibition therapy.

Additionally, the kit includes an antibody directed against a $PGE_2$ metabolite. Methods for the preparation and purification of antibodies are known in the art, and are described, for example, in Harlow et al., 1988, Antibodies: A Laboratory Manual, Cold Spring Harbor, N.Y. The antibody can be any type of antibody known in the art. The kit can, optionally include a secondary antibody directed against the antibody specific for the $PGE_2$ metabolite.

The kit can optionally include at least one sample container for containing a tissue or body fluid sample obtained from the mammal. The kit also optionally includes a solution useful in the extraction of a $PGE_2$ metabolite for cardiovascular risk from the tissue or body fluid sample obtained from the mammal.

Furthermore, the kit includes an instructional material for use in the assessment of cardiovascular risk in a mammal. The instructional material can be a publication, a recording, a diagram, or any other medium of expression which can be used to communicate the usefulness of the method of the invention in the kit for assessment of cardiovascular risk in a mammal. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

In another embodiment, the kit comprises a dipstick or means for a chromatographic immunoassay for measuring a $PGE_2$ metabolite.

The kit may further comprise components to enable assessing cardiovascular risk. Accordingly, the kit comprises a negative control solution containing a prostacylin or thromboxane metabolite at a concentration of about the concentration of the p prostacylin or thromboxane metabolite which is present in a tissue or body fluid sample of a mammal which is not at increased cardiovascular risk. The kit also includes a positive control solution containing a prostacylin or thromboxane metabolite at a concentration of about the concentration of the prostacylin or thromboxane metabolite which is present in a tissue or body fluid sample of a mammal which is at increased risk of cardiovascular risk.

Additionally, the kit includes an antibody directed against a prostacylin or thromboxane metabolite for cardiovascular risk. The kit can, optionally include a secondary antibody directed against the antibody specific for the prostacylin or thromboxane metabolite.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the experiments presented in the Experimental Examples below are now described.

In all the experiments, transgenic mice deficient in the indicated gene were compared with appropriate strain-, age-, and sex-matched control animals. The investigator was unaware of the genotype throughout the experiment. All procedures were approved and animal husbandry was overseen by the Institutional Animal Care and Usage Committee of the University of Pennsylvania.

Generation of PGHS-1 KD and PGHS-2$^{Y385F}$ mutant mice: PGHS-2$^{Y385F}$ mutant mice were generated using a homologous recombination strategy to replace Tyr-385 with phenylalanine (Yu et al., 2005a, J. Clin. Invest. (submitted manuscript)). Briefly, a 7.7 kb segment containing exons 1-9 was used as the 5' arm in the targeting construct cloned into a modified pPNT vector, upstream of a floxed neomycin cassette (Neo) using appropriate linkers. The mutation Phe385 to Tyr385 was induced with the QuickChange site-directed mutagenesis kit (QIAGEN®, Valencia, Calif.). A 3.5 kb fragment with exon 10 and 3' flanking sequence was then cloned downstream of the floxed Neo site to generate the final construct. TL1 ES cells were transfected with Not I-linearized targeting vector by electroporation, The targeted ES clones were injected into blastocysts derived from C57BL/6J mice, and germ-line transmission (PGHS2 Y385F$^{Neo}$) was confirmed first by Southern blot analysis and subsequently by genomic PCR and sequencing. The mice were maintained on a mixed C57BL/6×129/sv genetic background and the WT controls were generated from heterozygous PGHS-2$^{Y385F}$ mice.

Insertion of a Neo within intronic sequences can generate a hypomorphic allele or "knock down" (KD) of gene expression. PGHS-1 KD mice were generated by a Neo insertion in PGHS-1 intron 10, as described previously (Yu et al., 2005, J. Clin. Invest. 115: 986-95).

IP KO and mPGES-1 KO mice: IP KO mice were backcrossed into a C57BL/6 genetic background (Cheng et al., 2002, Science 296:539-541). IP$^{-/-}$, IP$^{+/-}$, and WT littermates were identified in litters generated by the intercross of IP$^{+/-}$ animals by polymerase chain reaction analysis (PCR) of genomic DNA isolated from tail biopsy samples. Southern blot analysis confirmed the IP gene copy number. mPGES-1 KO mice were kindly provided by Pfizer Inc. They were maintained on the DBA/1lacJ genetic background (Trebino et al., 2003, Proc. Natl. Acad. Sci. U.S.A. 100: 9044-9049) or on a mixed DBA/1lacJ×C57BL/6 genetic background. Heterozygous animals were intercroseed, and the litters were screened by PCR analysis to identify both mPGES-1 KO and wild-type controls. Biochemical and functional analyses in each case were performed on mutant mice and WT littermate controls.

Eicosanoid analyses: Urinary TxM and PGIM were measured in twenty four hour urines collected in metabolic cages. After extraction and purification by thin layer chromatography, they were analyzed by a stable isotope dilution reverse phase (C18) HPLC/tandem mass spectrometry assay and gas chromatography/mass spectrometry, respectively, as previously described (Egan et al., 2005, Circulation 111: 334-242).

Urinary PGEM was measured by LC/MS/MS as follows: First, 10 ng of hexadeuterated PGEM (9,15-dioxo-11α-hydroxy-2,3,4,5-tetranor-prostan-1,20-dioic-17,17,18,18,19,19-d$_6$ acid; Cayman Chemical Co., Ann Arbor, Mich.) was added as an internal standard to 0.1 ml of mouse urine. Next, 50 μL of 1 g/ml methoxyamine HCl was added, and the sample was mixed and allowed to stand at room temperature for 15 minutes. The sample was then diluted to 1.0 ml with water and loaded on a StrataX solid phase extraction (SPE) cartridge (Phenomenex, Torrance, Calif.). The SPE was eluted with 1.0 mL of 5% acetonitrile in ethyl acetate, dried, dissolved in 200 μL 10% acetonitrile in water, and injected for LC/MS/MS analysis. Transitions monitored were m/z 385→336 for the endogenous PGE-M and 391→342 for the internal standard.

Models of Thrombogenesis:

(i) Photochemical vascular injury: This model is an adaptation of one previously described method (Yu et al., 2005, J. Clin. Invest. 115:986-95). Briefly, mice were anesthetized with sodium pentobarbital (80 mg/kg, intraperitoneally). The left common carotid artery was isolated and a Doppler flow probe (Model 0.5 VB, Transonic Systems Co., NY) was applied. The probe was connected to a flowmeter (Transonic Model T105) and interpreted with a computerized data acquisition program (Powerlab, AD Instruments, CO). Just before i.v. injection of Rose Bengal (50 mg/kg body weight, Fisher Scientific, NJ), a 1.5-mW green light laser (540 nm) (Melles Griot Inc, Carlsbad, Calif.) was applied to the desired site of injury at a distance of 5 cm from the carotid artery. Blood flow was monitored up to 120 minutes after injection or until stable occlusion occurred. Stable occlusion was defined as a blood flow of 0 ml/min for 3 minutes. To confirm occlusive thrombosis, carotid arterial segments subjected to injury were excised and embedded in paraffin. Sections were then stained with hematoxylin and eosin.

(ii) Collagen induced platelet consumption: Briefly, mice (8 weeks old) were weighed and anesthetized with sodium pentobarbital (80 mg/kg). 100 μl of a mixture of collagen (250 μg/ml) and epinephrine (15 μg/ml) in 0.9% NaCl was injected rapidly into the tail vein. Blood was collected from the inferior vena cava after 2 minutes and anticoagulated with $\frac{1}{6}^{th}$ vol of tripotassium EDTA. After thorough mixing, platelets were counted by automated multispecies hematology analyzers (CDC Technologies), as previously described (Gresele et al, 1990, Thromb. Haemost. 64:80-6).

(iii) U46619 induced sudden death: This model is based on a model established previously (Momi et al., 2000, Eur. J. Pharmacol. 397: 177-85). Briefly, mice (3-4 months old) were anesthetized with sodium pentobarbital. Then they received a rapid intravenous injection of U46619 (0.2 mg/kg in PBS, Cayman Chemical) via the tail vein. Heart rate was monitored for 15 minutes prior to sacrifice. The mice which did not die within this time period were recorded as survivors.

(iv) Tail bleeding time: Bleeding time was measured by the tail clip method before and 6 hours after 2 mg/kg lipopolysaccharide (LPS; Sigma, St. Louis, Mo.) or saline vehicle were administered intraperitoneally to mice that were 10 to 12 weeks of age.

(v) Platelet aggregation assay: Blood was isolated from the inferior vena cava of anesthetized mice (80 mg/kg sodium pentobarbital) using a heparinized syringe (15 U/ml blood). 250 μl blood was mixed with 750 μl of sodium chloride at 37° C. Platelet aggregation was performed using a 500 Whole Blood Lumi-Aggregometion System (Chrono-Log Corp, Havertown, Pa.) as previously described (Gresele et al., 1983, Thromb. Haemost. 50: 852-6; Booth et al., 1998, Can. J. Physiol. Pharmacol. 76: 811-3; Emery et al., 1995, Arterioscler. Thromb. Vasc. Biol. 15: 748-53). Samples were pretreated with or without 10 nM cicaprost for 1 minute, and aggregation was initiated by addition of 2 μg/ml collagen.

Blood Pressure Measurements:

(i) Tail Cuff measurement: Resting systolic blood pressure was measured in conscious, 3-4 month old mice using a computerized, noninvasive tail-cuff system, BP-2000 Blood Pressure Analysis System™ (Visitech Systems, Inc. Apex, N.C.). The validity of this system has been demonstrated previously (Tilley et al., 1999, J. Clin. Invest. 103:1539-45; Kennedy et al., 1999, Nat. Med. 5: 217-20). Mice were adapted to the system for 14 days by taking blood pressure measurements during 25 minute long sessions. The sessions were held once daily between 15:00 and 18:00. After the adaptation period, blood pressure was recorded daily for 3 consecutive days in the same way. Data were collected and analyzed using updated BP 2000 Analysis Software.

(ii) Telemetry: This approach is based on prior studies with minor modifications (Carlson et al., 2002, Hypertension 39: 214-8; Carlson et al., 2000, Hypertension 35: E1-5). Briefly, male mice (12-16 weeks old) were anesthetized (intraperitoneal administration of 100 mg/ml ketamine and 5 mg/ml acepromazine) and were subject to surgery under strict sterile conditions. A horizontal incision, right blade to mid-scapular, was made on the back, and the telemetry probe (TA11-PA20; Data Sciences International, Arden Hills, Minn.) was inserted. The probe was secured by suturing the 3 suture holes on the probe to the skin, along with an additional suture which ran through the muscle and looped around the body of the probe and through the first suture hole. This additional suture prevented the probe from sliding laterally down the side of the mouse. A vertical incision was then made on the neck, and the tips of fine hemostats were advanced underneath the skin to the incision on the back and externalized. The flexible tip of the transmitter catheter was gently grasped and pulled through, so that it protruded through the incision on the neck. The left common carotid artery was then isolated. The tip of the catheter was inserted into the common carotid lumen, and advanced until the catheter notch reached the level of the carotid bifurcation. The transmitter signal was monitored with an AM radio tuned to the low end of the dial to verify proper catheter placement. A pulsing tone indicated proper catheter placement.

After surgery, mice were maintained on normal salt intake (0.6% NaCl; diet No. 8746, Harlan Teklad, Indianapolis, Ind.) for a 1-week period, after which the telemetry probes were turned on. The cage with the animal was placed on a receiver plate, and the signal collected using the Dataquest LabPRO Acquisition System, version 3.01 (Data Sciences international, Inc.). Mice were maintained on a 12 hour light: dark regimen, and in a sound attenuated room. 10 second waveforms of mean arterial pressure (MAP), diastolic arterial pressure (DAP), systolic arterial pressure (SAP), heart rate (HR), and locomotor activity were sampled every 5 minutes during the 4 day monitoring periods. 12-hour average over the 4 days was calculated and used to represent daytime (resting phase)/nighttime (active phase) blood pressure.

(iii) Direct measurement of blood pressure: Mice were anesthetized (ketamine 100 mg/kg, acepromazine 5 mg/kg) and placed on a temperature-controlled panel. The right internal jugular vein and left carotid artery were cannulated with PE-10 tubing. The arterial catheter was connected to a Capto SP844 pressure transducer (Capto, Horten, Norway), and blood pressure (BP) was monitored continuously with a Powerlab/8SP system (AD Instruments Inc, Colorado Springs, Colo.), as previously described (Hui et al., 2004, Circulation 110: 3360-6; Rocca et al., 2000, Nat. Med. 6: 219-21). Blood pressure and heart rate were continuously monitored for 20-40 min until stable values were obtained. After the equilibration period and the baseline BP was recorded, mice were injected via the right internal jugular vein with cicaprost (1 µg/kg in 4 ml/kg saline) as a bolus. The same volume of saline was injected before cicaprost administration to exclude volume-mediated BP changes. The BP was continuously recorded until it returned to pretreatment baseline.

Statistical analysis: Statistical analyses were performed by one way ANOVA, followed by a pairwise comparison and/or adjustment for multiple comparisons, as appropriate and using a computerized software package (GraphPad Prism version 4.0). All values were expressed as mean±SEM. A value of P<0.05 was considered significant.

mPGES-1, LDLR DKO mice: The protocol was approved by the Institutional Animal Care and Usage Committee. mPGES-1 knock outs were generated as described elsewhere herein. Female LDL receptor KOs (LDLR KOs) were obtained from Jackson Laboratories (Bar Harbor, Me.; 10th generation back-crossed from 129/B6F1 heterozygous to C57 B1/6). DKO mice were generated using a simple breeding strategy and were fed a high fat, Western-type diet (0.2% cholesterol, 21% saturated fat; formula TD88137, Harlan Teklad, Madison, Wis.) from six weeks of age. The diet was replaced every three days.

After three months, half of the mice were euthanized by overexposure to $CO_2$. Those remaining were fed for a further three months to examine both early and late stages of atherosclerosis. Mean blood pressure was measured by ambulatory monitoring over a continuous 24 hour period.

Aortic en face analysis: The aorta was perfused for 10 minutes with PBS by inserting a cannula into the left ventricle and allowing free efflux from an incision in the vena cava. The vessel was opened longitudinally from the aortic root to the iliac bifurcation after removal of the surrounding adventitial tissue and fixed overnight at 4° C. in 10% phosphate buffered formalin (Fisher Scientific, Atlanta, Ga.). Finally, aortas were stained with Sudan IV (Sigma-Aldrich, St. Louis, Mo.). The extent of atherosclerosis was determined using the en face method (Morishita et al., 1990, J. Clin. Invest. 86: 1885-91).

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Experimental Example 1

Assessment of PGHS Enzymes Contribution to $PGI_2$ and Tx Biosynthesis

The relative contribution of the PGHS enzymes, PGHS-1 and PGHS-2, to the biosynthesis of $PGI_2$ and $TxA_2$ was assessed by measuring urinary 2,3-dinor 6-keto $PGF_{1\alpha}$ (PGIM) and 2,3-dinor $TxB_2$ (TxM) respectively. PGIM and TxM were measured in mice deficient in PGHS-1 (PGHS-1 KO) or PGHS-2 (PGHS-2 KO) and in mice treated with either celecoxib or 5,5-dimethyl-3-(3-fluorophenyl)-4-(4-methylsulphonyl)phenyl-2(5H)-furanone (DFU), both of which are highly selective PGHS-2 inhibitors. PGIM and TxM was also assessed in PGHS-1 knockdown (KD) mice. PGHS-1 KD mimics the effect of low dose aspirin, achieving a mean 97% inhibition of platelet Tx formation (Yu et al., 2005, J. Clin. Invest. 115:986-95). Traditional NSAIDS and NSAIDs selective for PGHS-2 inhibit COX activity, not POX activity. Tyr385 in PGHS (ovine PGH-1 numbering) is critical for cyclooxygenase (COX) catalysis, but is uninvolved in peroxidase (POX) activity. PGIM and TxM was also assessed in PGHS-$2^{Y385F}$ mice, in which the cyclooxygenase, but not the peroxidase (POX) function, of PGHS-2 is inactivated, thereby mimicking the effect of a selective PGHS-2 inhibitor (Yu et al., 2005a, J. Clin. Invest. (Submitted manuscript)).

Figure 2:
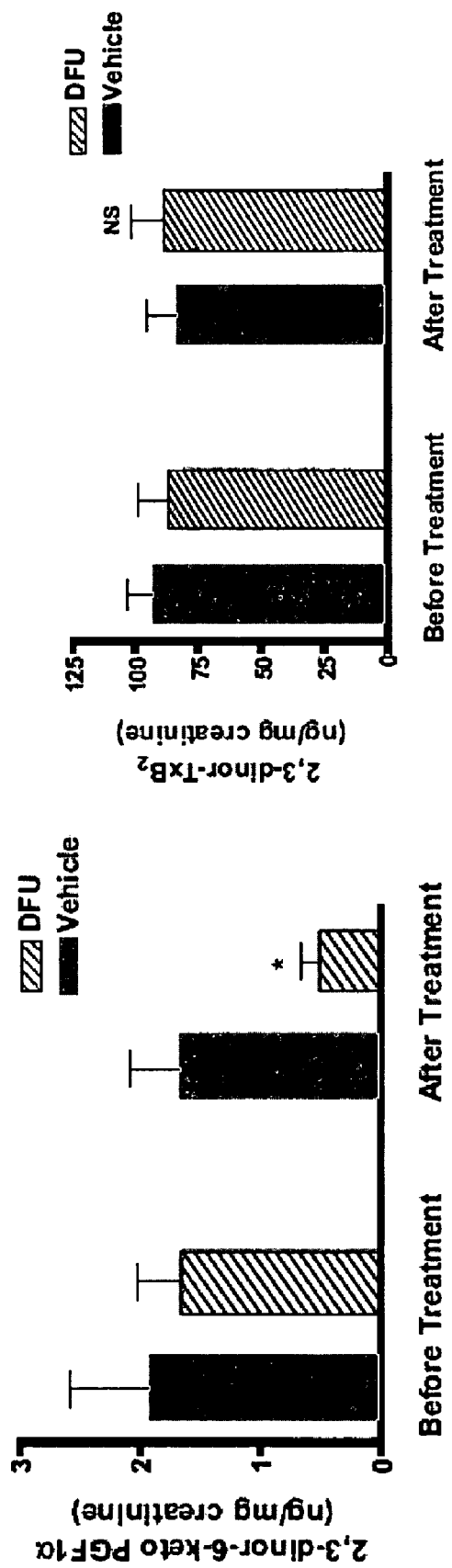
FIG. 2 is a series of graphs depicting the amount of two urinary prostaglandin metabolites, PGIM and TxM, before and after administration of DFU, a PGHS-2 specific inhibitor, to WT male mice. (*P<0.05 compared to pre-administration value; NS=not significant; 9-13 animals in each group)

Urinary excretion of 2,3-dinor $TxB_2$ (TxM) is decreased significantly (n=6; * P<0.001) from values in wild type (WT) mice by PGHS-1 deletion (KO) or knock down (KD), but not in PGHS-2 KO or PGHS-$2^{Y385F}$ mice or those treated with the PGHS-2 inhibitor celecoxib (100 mg/kg/day for 30 days on a mixed C57BL/6×129/sv genetic background) or DFU. (FIGS. 1 and 2). In contrast, urinary 2,3-dinor 6-keto $PGF_{1\alpha}$ (PGIM) is depressed significantly in PGHS-2 KO and PGHS-$2^{Y385F}$ mice and by treatment with celecoxib or DFU, but not in PGHS-1KO or KD mice (FIGS. 1 and 2). Thus, as in humans, PGHS-1 is the dominant source of TxM and PGHS-2 is the dominant source of PGIM in mice.

Experimental Example 2

Cardiovascular Effect of Prostacylin Receptor (IP) Deletion

Figure 3:
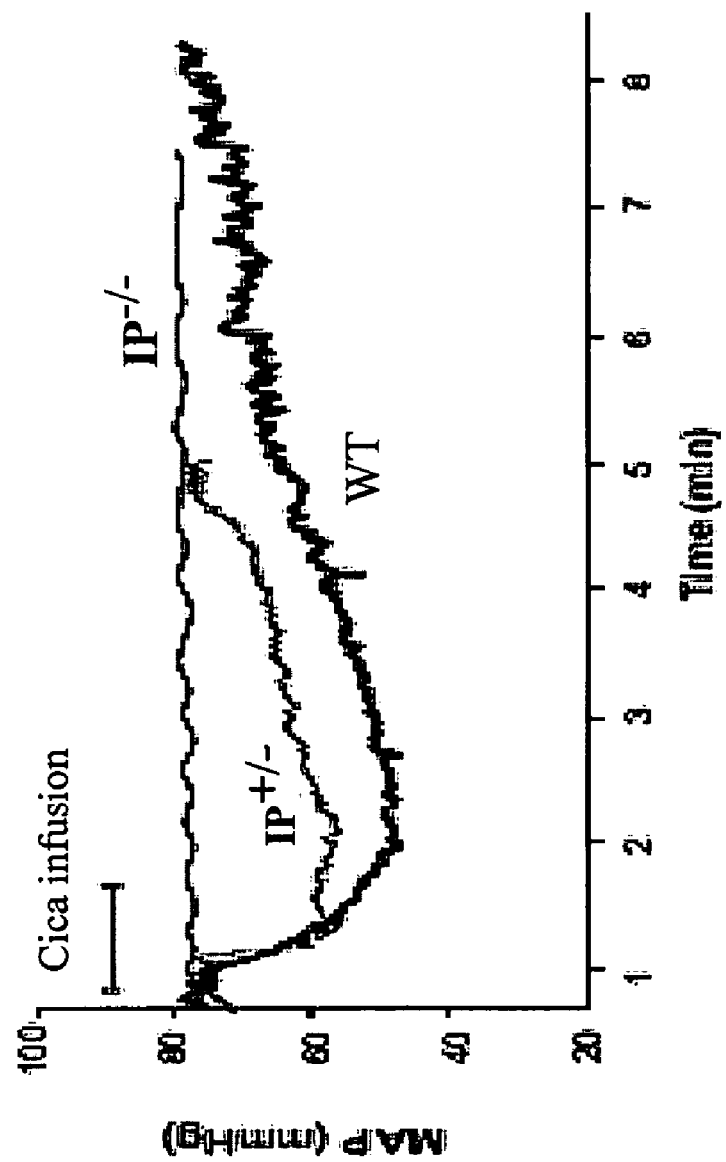
FIG. 3 depicts representative mean arterial pressure (MAP) tracings measured in WT, $IP^{+/-}$, and $IP^{-/-}$ littermates following intravenous administration of the IP agonist cicaprost (Cica).
Figure 4:
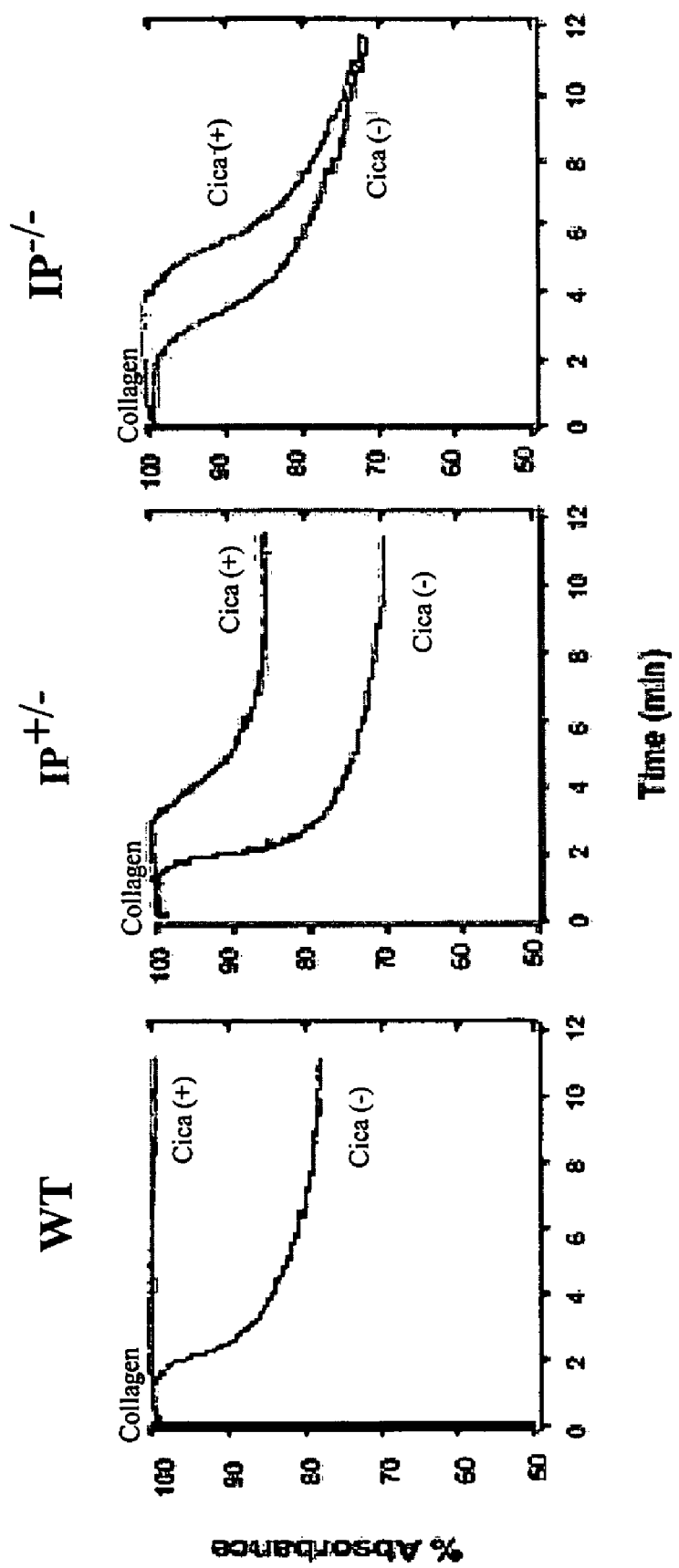
FIG. 4 is a series of images depicting representative platelet aggregation tracings of whole blood from WT, $IP^{+/-}$, and $IP^{-/-}$ littermates on C57BL/6 genetic background pretreated with (+) or without (−) 10 nM Cica. Aggregation was initiated by addition of 2 μg/ml collagen.
Figure 5:
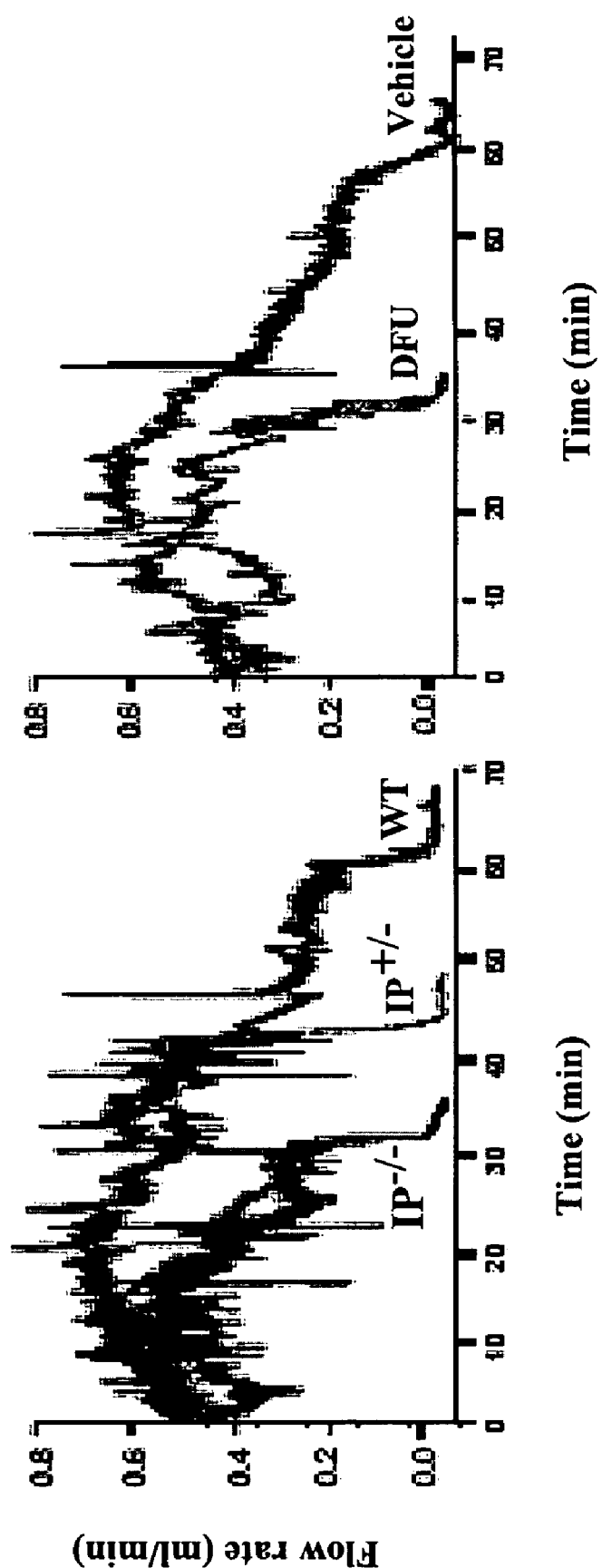
FIG. 5 is a series of graphs depicting representative carotid artery blood flow recordings after photochemical injury. The left panel is data for WT, $IP^{+/-}$, and $IP^{-/-}$ mice on C57BL/6 genetic background. The right panel is data for WT mice treated with DFU (10 mg/kg/day for 3 days) or vehicle. Rose Bengal dye was injected at time=0 min.

The cardiovascular consequences of deleting just one copy of the IP on cardiovascular function in vivo was studied. Mean arterial pressure (MAP) was measured directly via carotid artery catheterization in anesthetized WT, $IP^{+/-}$, and $IP^{-/-}$ littermates on C57BL/6 genetic background, following administration of the IP agonist cicaprost (Cica) 1 µg/kg intravenously (FIG. 3). The maximal decline evoked by Cica in MAP was 36±3.5% from pretreatment baseline in WT, 24%±3.3% in IP+/− and 0% in IP−/− littermates(F=42, n=5; P<0.0001). Similarly, the duration of the depressor response fell from 10.8±2.5 min in WTs to 5.3±1.1 min in IP+/− animals; there was no change in MAP in IP−/− mice (F=12, n=5, P<0.005). A similar effect of IP deletion was seen on the inhibitory effect of 10 nM cicaprost on platelet aggregation induced by collagen 2 µg/ml ex vivo (FIG. 4). IP+/− mice attained 86.7% of the maximal inhibition observed in WTs, while the inhibition was not achieved in IP−/− mice (F=744, n=5-9; P<0.0001). The impact of IP deletion on the time to thrombotic carotid arterial occlusion, induced by green laser activation of Rose Bengal, which causes free radical catalyzed vascular injury, was also gene-dose dependent (FIG. 5, left panel). The time to occlusion fell from 66.3±5.1 min in WTs to 44.4±7.0 ml in $IP^{+/-}$ to 29.7±7.6 min in $IP^{-/-}$ mice (F=6.5, n=9-10, P<0.0055). Inhibition of PGHS-2 by DFU also accelerated thrombogenesis, from 59.4±10.4 min to 33.4±4.3 min (n=7-8, P<0.05; FIG. 5, right panel). Thus, the mean impact of DFU on time to occlusion (56.2% of WT value) was intermediate between that of $IP^{+/-}$ (68.1% of WT) and $IP^{-/-}$ (45.5%) mice.

Experimental Example 3

PGHS-2 and Thrombosis

Figure 6:
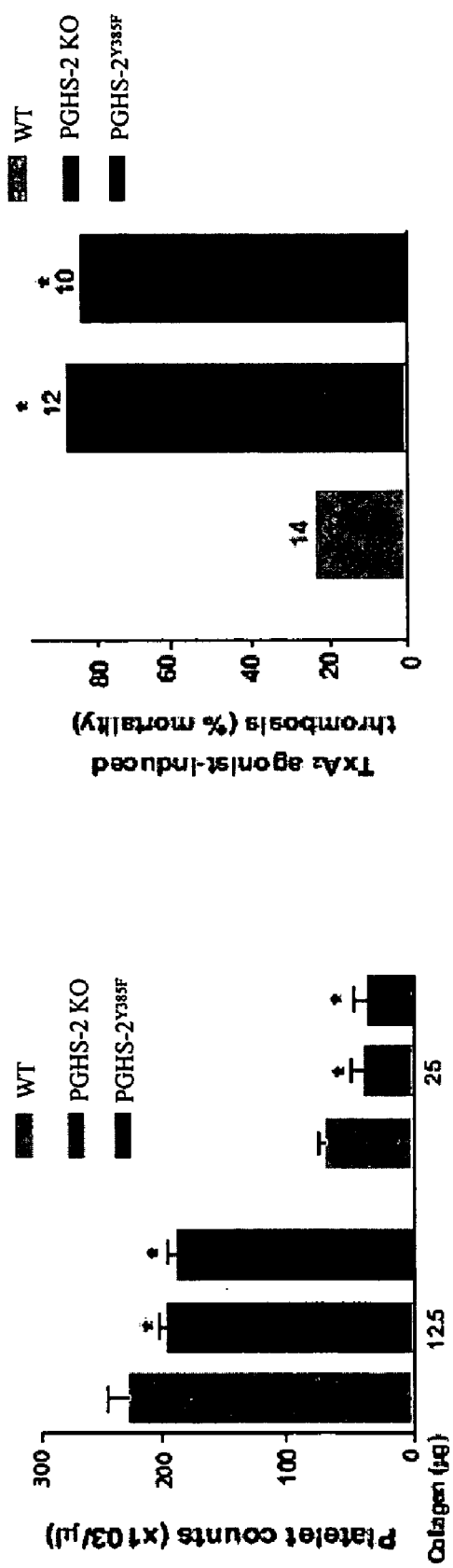
FIG. 6 is a series of two graphs depicting the effect of PGHS-2 inhibition or deletion on circulating platelet counts and on sudden death. The left panel data is circulating platelet number 2 min after i.v. injection of collagen (12.5 and 25 μg/kg) plus epinephrine (15 μg/ml, 100 μl) into 8-10 week old WTs, PGHS-$2^{Y385F}$, and PGHS-2 KO mice on a mixed C57BL/6×129/sv genetic background. The right panel data is the percent of mortality induced within 15 min by intravenous injection of 0.2 mg/kg of the $TxA_2$ analog, U46619.

Injection of the platelet agonist collagen results in a decrease in platelet count due to platelet consumption in a developing thrombus. As shown in FIG. 6 (left panel), there is a dose-dependent decrease in platelets in WTs, PGHS-$2^{Y385F}$, and PGHS-2 KO mice. The dose-dependent decrease is significantly greater (n=4, * P<0.01) in mice in which PGHS-2 is deleted or mutated than in WT mice. Intravenous injection of U46619, a $TxA_2$ analog and thromboxane receptor (TP) agonist, can induce sudden death. The frequency of sudden death induced by an intravenous dose of U46619 was augmented in PGHS-2 KO and PGHS-$2^{Y385F}$ mice compared to WT mice (n=10-14, * P<0.01) (FIG. 6, right panel).

Furthermore, the prolongation in bleeding time—an index of platelet vessel wall interactions—induced by LPS (2 mg/kg i.p.) administration to WT mice (2.0±0.2 min vs 8.9±2.0 min, n=14; P<0.001), was abolished in PGHS-$2^{Y385F}$ mice (1.99±0.2 7 min vs 2.3±0.78 min, n=6-7; P=NS).

Figure 7:
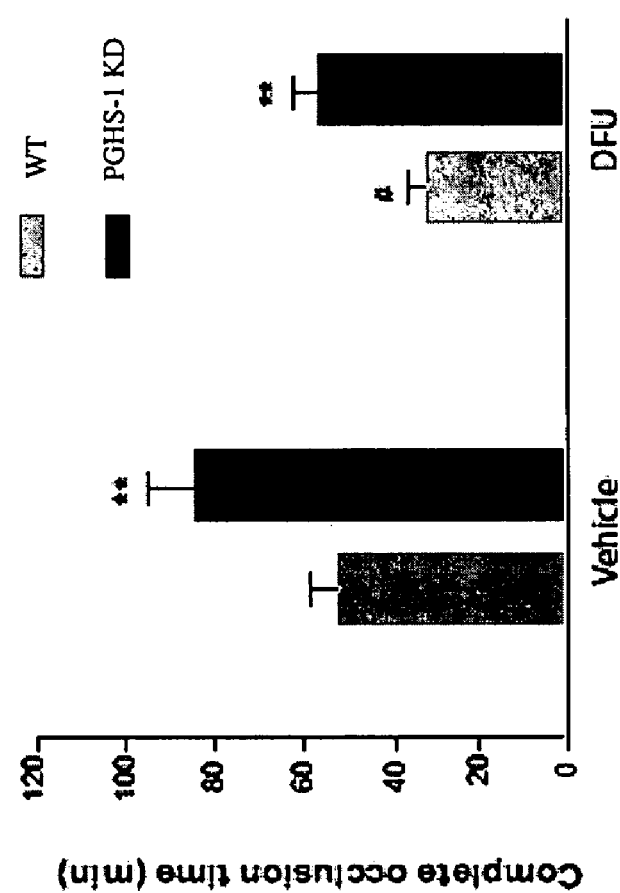
FIG. 7 is a graph of time to complete occlusion as a function of PGHS enzymes. (** P<0.01; # P<0.05). 10-12 animals were used in each group and all of them were on a mixed C57BL/6×129/sv genetic background.

Acceleration of the time to thrombotic carotid vascular occlusion with the PGHS-2 inhibitor, DFU, was attenuated by PGHS-1 KD (FIG. 7). The time to thrombotic occlusion of the carotid artery after free radical catalyzed dependent vascular injury is delayed in PGHS-1 KD mice compared to WTs (left panel;  P<0.01). PGHS-2 inhibition with DFU (10 mg/kg) accelerates the time to occlusion (# P<0.05) compared to vehicle treated WTs. The time to occlusion in DFU treated animals is delayed in PGHS-1 KDs compared to WTs ( P<0.01), while the time to occlusion in DFU treated PGHS-1 KDs does not differ significantly from that in vehicle treated WT controls. This result suggests that the risk of thrombosis from selective inhibition of PGHS-2 would be attenuated, but not abolished, by concurrent low dose aspirin therapy.

Experimental Example 4

Assessment of PGHS Enzymes and Hypertension

Figure 8:
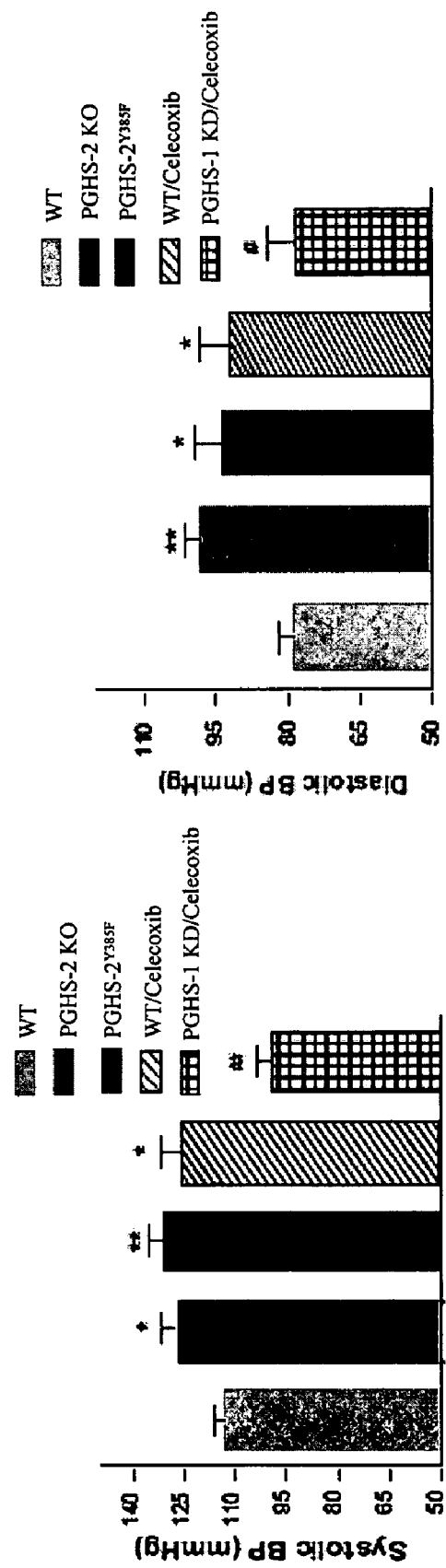
FIG. 8 is a series of two graphs depicting the effect of PGHS-2 disruption or inhibition on blood pressure. Both systolic (left panel) and diastolic (right panel) blood pressure were measured by tail cuff.

Blood pressure was elevated by PGHS-2 deletion or mutation or by treatment with the PGHS-2 inhibitor, celecoxib compared to WT controls on a regular chow diet. The hypertensive effect of celecoxib was attenuated by PGHS-1 KD (FIG. 8). Both systolic (left panel) and diastolic (right panel) blood pressure, as measured by tail cuff, were elevated significantly in 3 month old PGHS-2 KO, PHGS$^{Y385F}$ and celecoxib treated mice as compared to WTs on a mixed C57BL/6×129/sv genetic background (n=6-12, * P<0.05; **, P<0.01). In PGHS-1 KDs (n=7), the hypertensive effect of celecoxib is attenuated compared to WTs (# P<0.05, ## P<0.01).

Thus, selective disruption or deletion of PGHS-2 can result in an elevation of blood pressure in mice, and this is attenuated by mimicking genetically the impact of low dose aspirin. This is comparable to the effect of deletion of the IP (Francois et al., 2005, Cell Metab. 2:201-207). This effect contrasts with the impact of TP deletion on the hypertensive response to IP deletion. While disruption of the TP prevents the consequent myocardial injury, it does not alter the rise in blood pressure in IP KOs (Pini et al., 2005, Arterioscler. Thromb. Vasc. Biol. 25:315-20).

These results suggest the importance of suppression of products additional to $PGI_2$ (such as $PGE_2$ acting via the EP2 or $PGD_2$ acting via DP1) in the hypertensive response to PGHS-2 inhibition or disruption and/or the role of suppressing products additional to $TxA_2$ (such as $PGE_2$ acting via EP1 or $PGF_{2\alpha}$ acting via the FP) in the antihypertensive impact of PGHS-1 KD.

Experimental Example 5

Figure 9:
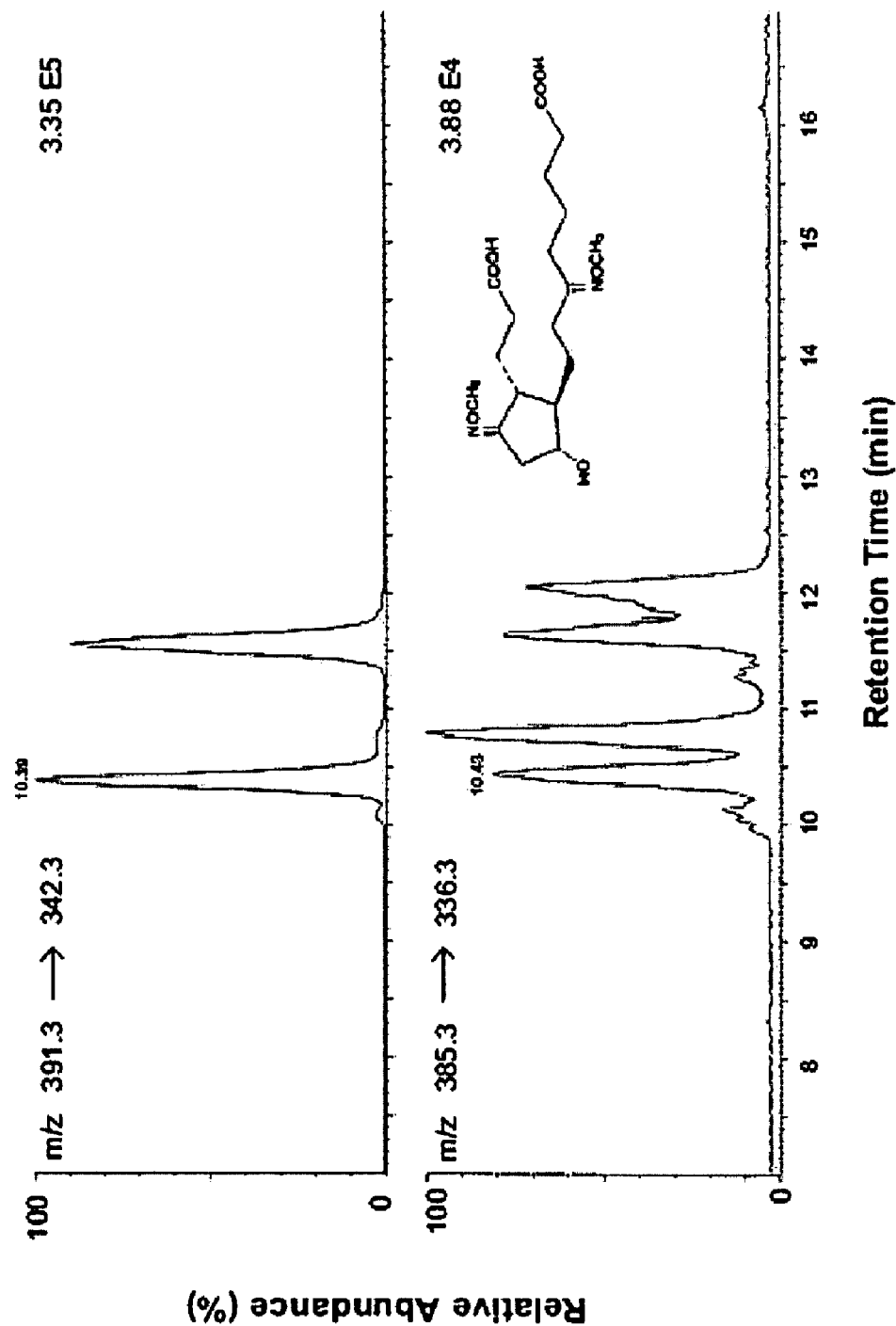
FIG. 9 depicts selected ion monitoring traces of the methoximated derivative of endogenous PGEM (9,15-dioxo-11α-hydroxy-2,3,4,5-tetranor-prostan-1,20-dioic-17,17,18,18,19,19-$d_6$ acid; bottom tracing) and its hexadeuterated internal standard (top tracing).
Figure 10:
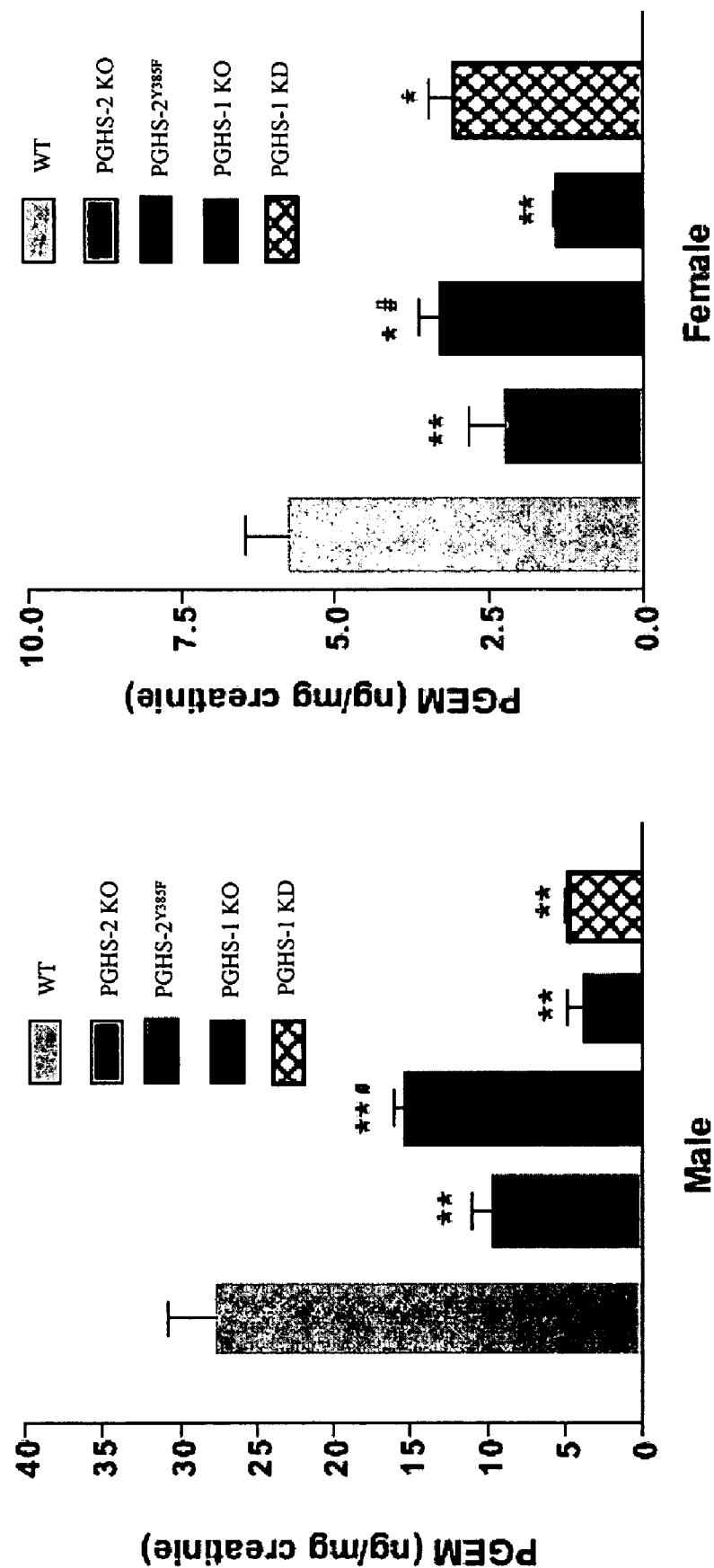
FIG. 10 is a series of two graphs depicting PGEM biosynthesis in relation to PGHS-1 disruption or knockdown and PGHS-2 disruption or mutation in male (left graph) and female (right graph) mice.
Figure 11:
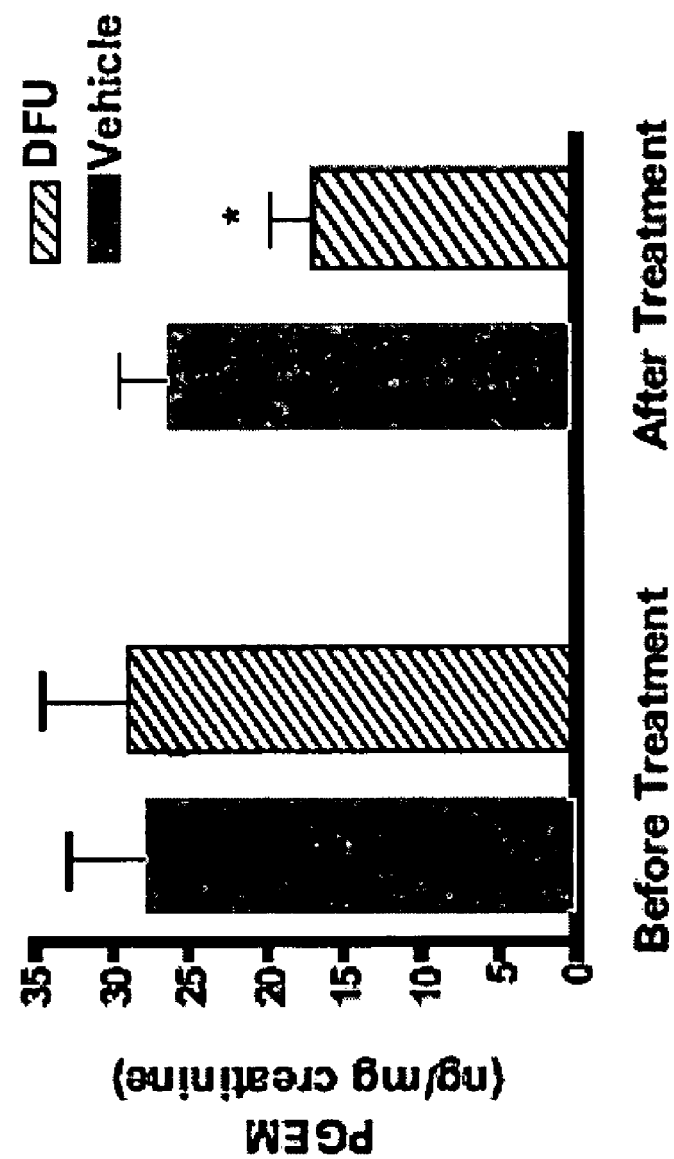
FIG. 11 is a graph of the amount of urinary PGEM in WT male mice after administration of DFU. (*P<0.05 compared to pre-administration value; 9-13 animals in each group)

Assessment of PGHS Enzymes and $PGE_2$ Biosynthesis $PGE_2$ biosynthesis was assessed in mice having inhibited or deleted PGHS-1 or PGHS-2 function using a mass spectrometric assay (FIG. 9) for the major PGE metabolite, 11α-hydroxy-9,15-dioxo-2,3,4,5-tetranor-prostane-1,20-dioic acid (PGEM). Urinary PGEM decreased significantly in both male and female PGHS-2 KO or PGHS-$2^{Y385F}$ mice compared to WT control on a mixed C57BL/6×129/sv genetic background (n=5-6; P<0.05, ** P<0.001). PGEM was also significantly lower in PGHS-1 KDs and PGHS-1 KOs compared to WTs of mixed C57BL/6×129/sv genetic background, (n=5-6; * P<0.05, ** P<0.001). PGEM was significantly higher in PGHS-$2^{Y385F}$ mice compared to PGHS-2KO (# P<0.05) on the same genetic background (FIGS. 10 and 11). Thus, it was observed that PGHS-1 KO or KD, as well as PGHS-2 KO, mutation or inhibition (by DFU) depressed PGEM significantly (FIGS. 10 and 11). Thus, unlike $PGI_2$ biosynthesis, both PGHS-1 and PGHS-2 each contribute substantially to $PGE_2$ biosynthesis.

Experimental Example 6

Assessment of mPGES-1 and $PGE_2$ Biosynthesis

Figure 12:
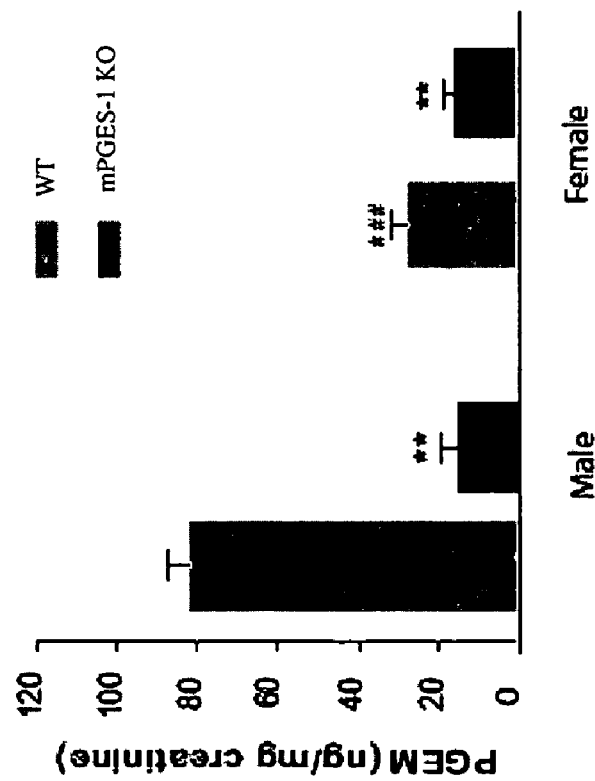
FIG. 12 depicts a graph of biosynthesis of $PGE_2$ in wild type and mPGES-1 knock out mice. (** p<0.01 compared to WT; ####P<0.001 compared to male WT).

Biosynthesis of PGE2 was assessed in mice in which the mPGES-1 was knocked out (FIG. 12). Urinary PGEM is significantly lower in both male and female (** $P<0.01$) mPGES-1 KO mice than in WT littermates (n=8-11 per group) on a DBA/1lacJ genetic background. Urinary PGE-M was also significantly higher in WT males than in females (####$P<0.001$). The mPGES-1 enzyme, which is known to colocalize with both PGHS enzymes, was thus determined to be a major source of urinary PGE-M.

Figure 13:
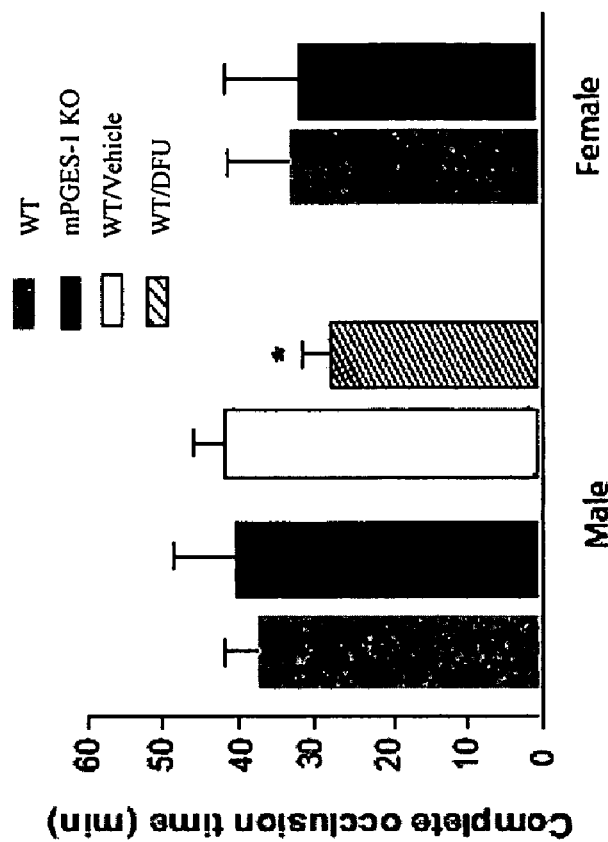
FIG. 13 is a graph of the time to carotid arterial thrombotic occlusion after photochemical injury in either male or female mice versus WTs littermates. DFU administered at 10 mg/kg. both on a DBA/1lacJ genetic background (n=6-10, P=0.85). PGHS-2 inhibition with DFU (10 mg/kg) accelerates the time to occlusion (#P<0.05) compared to vehicle treated WTs (n=10, *P<0.05).

The time to carotid arterial thrombotic occlusion after photochemical injury was assessed male and female mice versus WTs littermates, both on a DBA/1lacJ genetic background (n=6-10, P=0.85; FIG. 13). PGHS-2 inhibition with DFU accelerated the time to occlusion (#$P<0.05$) compared to vehicle treated WTs (n=10, *$P<0.05$). Unlike inhibition of PGHS-2, deletion of mPGES-1 failed to alter thrombogenesis in mice of either gender.

Figure 14:
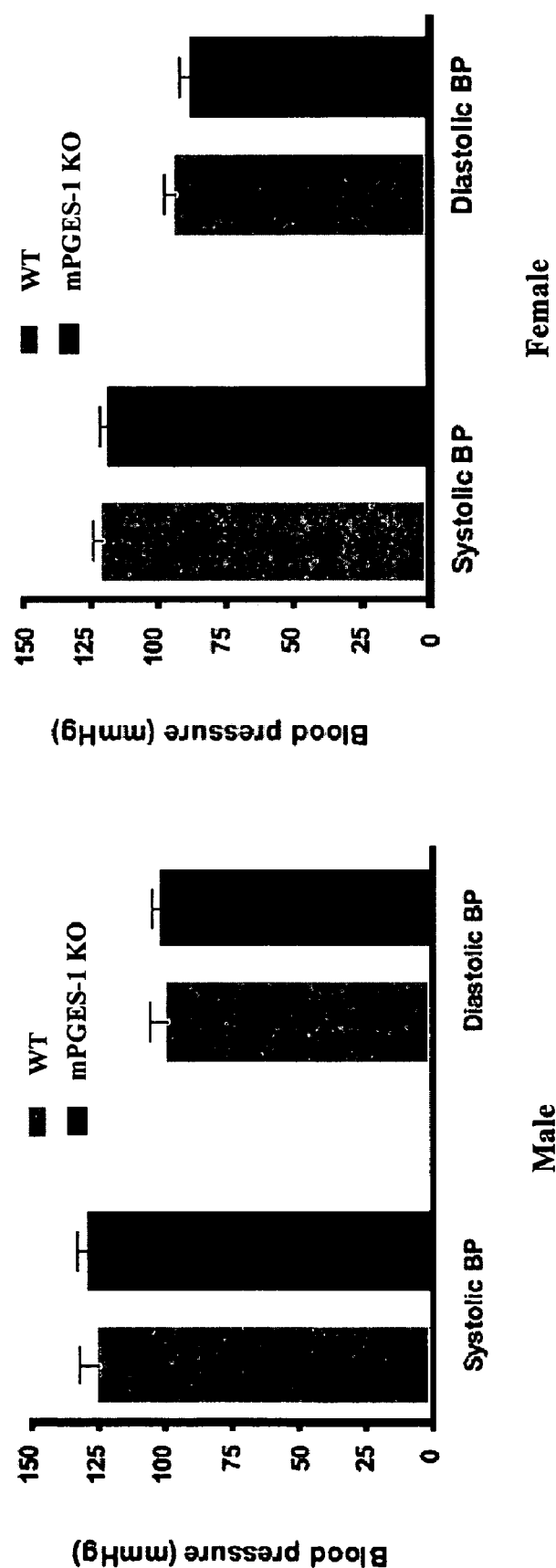
FIG. 14 is a series of graphs depicting the blood pressure in WT and mPGES-1 KO male and female mice. Blood pressure was measured by tail cuff. Mice were treated with normal salt diet. (0.6% NaCl, n=12 for each group)
Figure 15:
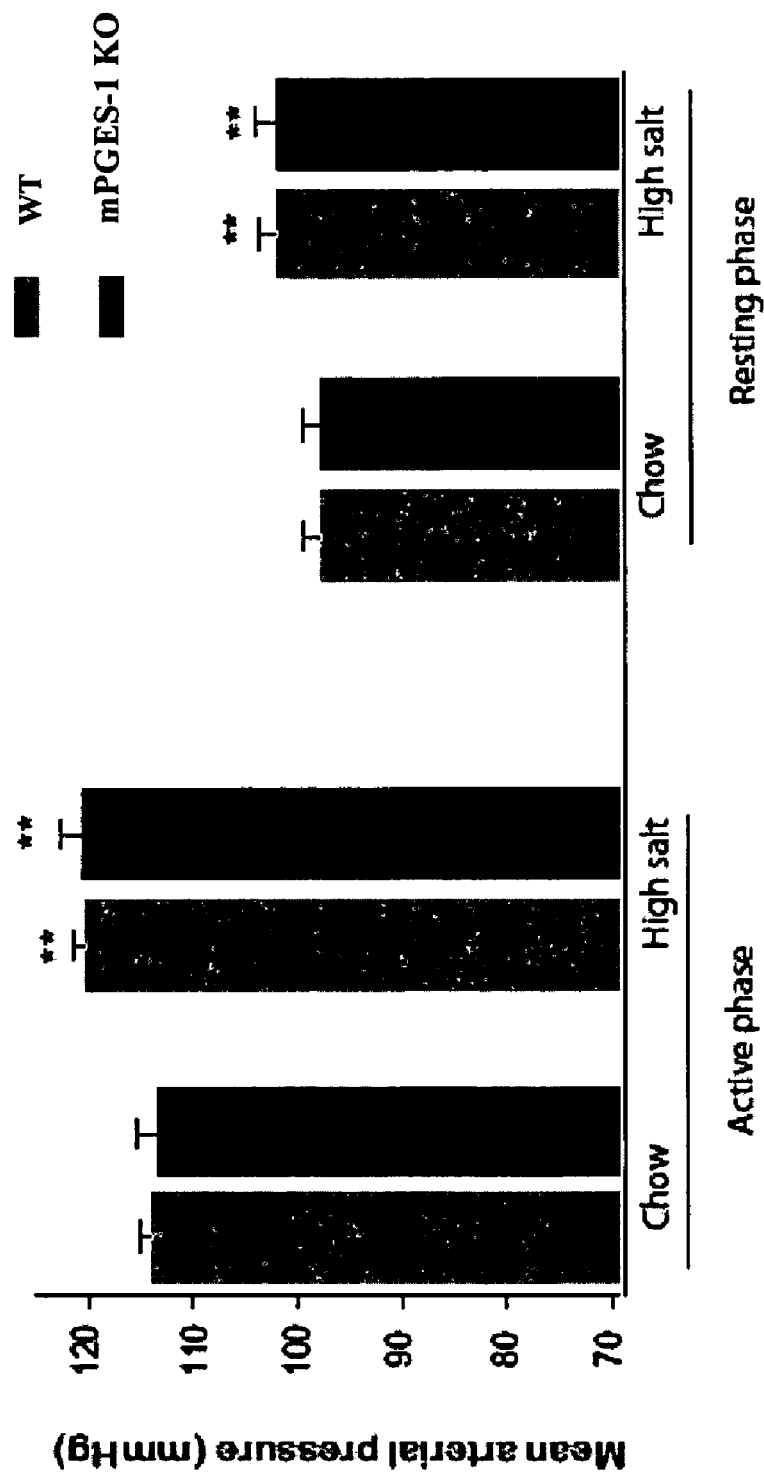
FIG. 15 is a graph depicting blood pressure in mPGES-1 KO mice on normal and high salt diets and at different times of day. Radio telemetry was used to measure continuously blood pressure. The recordings of the 12 h dark and light periods were classified as "active" and "resting", respectively. Blood pressure for each of these phases was averaged over consecutive four day periods for each mouse.

The impact of mPGES-1 deletion was studied by both tail cuff (FIG. 14) and telemetric approaches (FIG. 15). Blood pressure oscillated with a diurnal variation in both mPGES-1 KOs and WT littermates, both on a mixed DBA/1lacJ X C57BL/6 genetic background. Blood pressure was assessed continuously in male mice on both normal (0.6% NaCl) and high salt (8% NaCl) diets. Mean arterial pressure was higher (n=6, $P<0.01$) during the activity phase for both WT and mPGES-1 KO mice. A high salt diet induced a mean ~6% increase in mean arterial blood pressure in both WT and KO groups which was significant (** $P<0.01$), but no significant difference was apparent between the KOs and the WT mice. Thus, an impact of mPGES-1 deletion was not detected.

Figure 16:
FIG. 16 is a series of graphs depicting urinary PGIM and PGIM levels in mPGES-1 KO mice. Measurements were made in male littermates on a normal salt diet, and both on a mixed DBA/11acJ×C57BL/6 genetic background.

Deletion (or inhibition) of a PG synthase enzyme may result in an accumulation of the PGHS product, $PGH_2$, thus rendering it available for rediversion to other vasoactive PG synthases. Such a rediversion has been observed previously in an in vitro system, but has not been addressed in vivo. To test whether deletion of inhibition of mPGES-1 affected production of prostacylin or thromboxane in vivo, the urinary excretion of PGEM, PGIM and TxM was measured in mPGES-1 KO and WT male mice. TxM was unaltered by mPGES-1 deletion (335.7±43.4 ng/mg creatinine in WTs vs 359.7±52.5 ng/mg creatinine in KOs, n=14-17 mice per group; P=0.98). PGEM decreased significantly (n=8,*** $P<0.001$) in the KOs compared to WTs. Notably, PGIM increased significantly (n=8, *$P<0.05$) in the KOs compared to the WTs. See FIG. 16. Thus, $PGI_2$ biosynthesis was increased significantly in mPGES-1 KO mice.

Experimental Example 7

Assessment of Artherogenesis in mPGES-1, LDLR DKO Mice

Male mice lacking the LDL receptor (LDLR KO) develop atherosclerosis more rapidly on a high-fat diet than female LDLR KO mice (Tangirala et al., 1995, J. Lipid. Res. 36:2320-2328). Male and female mice knocked out for both mPGES-1 and LDLR (DKOs) were generated to examine the effect of suppressed $PGE_2$ on atherogenesis in these mice. DKOs and their WT littermates were maintained on a high-fat diet for 3 months or 6 months. At 3 and 6 months, blood pressure and en face aorta analysis were performed.

Figure 17:
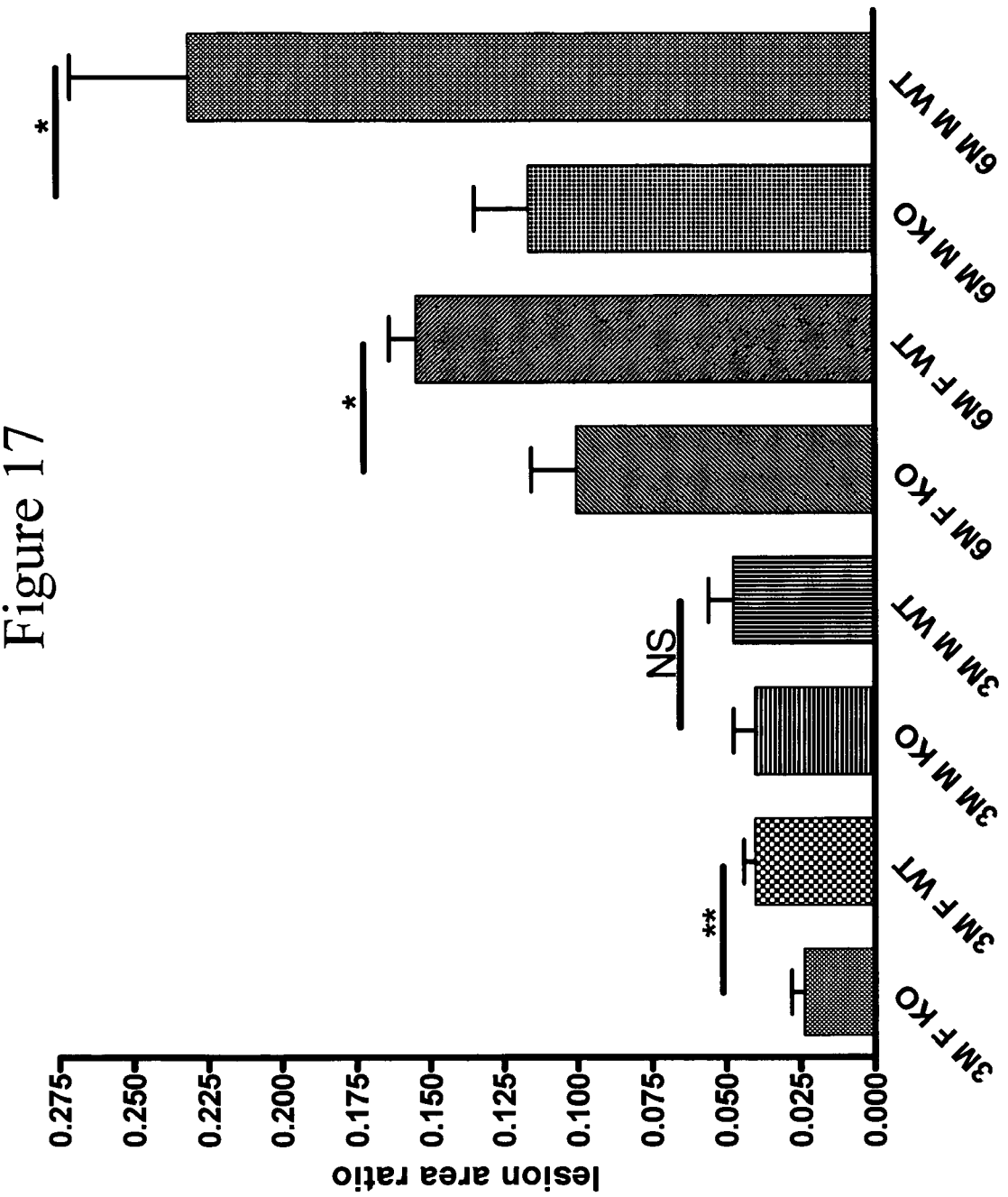
FIG. 17 is a graph of aortic en face data of mPGES-1-LdlR double knock out (DKO) and WT littermates, fed with a high fat diet for 3 months (3M) or 6 months (6M). Female (F) and male (M) mouse data shown separately. (NS=not significant; * P<0.05; ** P<0.01?; 10-15 animals in each group)
Figure 18:
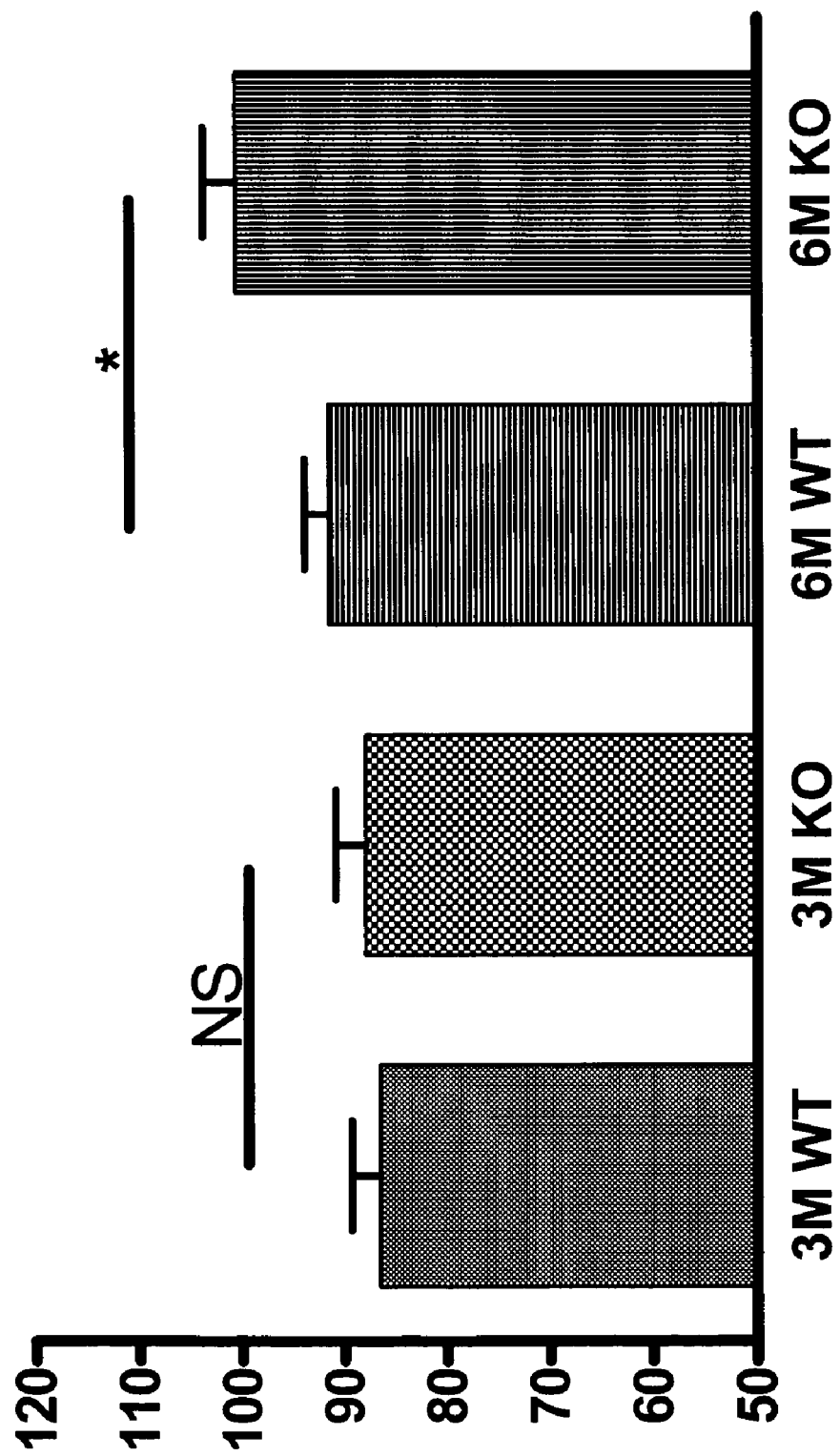
FIG. 18 is a graph of eman blood pressure of mPGES-1-LdlR DKO and WT littermates at 3 month and 6 months on a high fat diet. (NS=not significant; * P<0.05; X-Y animals in each group)

Analysis of aortas en face revealed that the extent of atherosclerosis did not differ significantly in male mice at 3 months (FIG. 17). In female mice, DKOs had a significantly smaller lesion area ratio than WT ($P<0.05$). At 3 months, the blood pressure of the DKO mice was comparable to that of the WT littermates (FIG. 18).

Remarkably, at 6 months on the high-fat diet, both male and female DKOs had significantly smaller lesion area ratios compared to their WT counterparts ($P<0.01$; FIG. 17). These data support that inhibition of mPGES-1 and the corresponding suppression of $PGE_2$ actually reduces the rate of atherogenesis. At 6 months, there was a modest but significant, increase in blood pressure in the DKO male mice, but not female mice, compared to their WT counterparts (FIG. 18). The significance and persistance of this increase is unknown.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of identifying an inhibitor of microsomal prostaglandin E synthase (mPGES-1) in a cell that does not increase risk of a cardiovascular event in an individual comprising said cell, the method comprising:
   a. measuring a first level of prostacyclin and a first level of prostaglandin E2 (PGE2) produced by a cell that expresses mPGES-1,
   b. administering a test compound to the cell, and
   c. measuring a second level of prostacyclin and a second level of PGE2 produced by the cell, wherein a test compound that reduces the second level of PGE2 compared to the first level of PGE2 and wherein the second level of prostacyclin is greater than the first level of prostacyclin is identified as an inhibitor of mPGES-1 that does not increase the risk of a cardiovascular event in an individual when administered to the individual.

2. The method of claim 1, wherein the cell is an endothelial cell.

3. The method of claim 2, wherein the endothelial cell is a murine endothelial cell or a human endothelial cell.

4. The method of claim 2, wherein the murine endothelial cell comprises a human mPGES-1 gene.

5. A method of identifying an inhibitor of microsomal prostaglandin E synthase (mPGES-1) that does not increase the risk of a cardiovascular event in an organism, the method comprising:
   a. measuring a first level of prostacyclin and a first level of prostaglandin E2 (PGE2) in a biological sample derived from an organism that expresses mPGES-1,
   b. administering a test compound to the organism, and
   c. measuring a second level of prostacyclin and a second level of PGE2 in a biological sample derived from the organism, wherein a test compound that reduces the second level of PGE2 compared to the first level of PGE2, and wherein the second level of prostacyclin is greater than the first level of prostacyclin, is identified as an inhibitor of mPGES-1 that does not increase the risk of a cardiovascular event in the organism when administered to the organism.

6. The method of claim 5, wherein the first and second levels of PGE2 and prostacyclin are measured in urine samples obtained from the organism.

7. The method of claim 5, wherein the organism is a mouse.

8. The method of claim 7, wherein the mouse expresses human mPGES-1.

* * * * *

SEQUENCE LISTING

```
<160> NUMBER OF SEQ ID NOS: 12

<210> SEQ ID NO 1
<211> LENGTH: 1805
<212> TYPE: DNA
<213> ORGANISM: Homo sapiens
<220> FEATURE:
<221> NAME/KEY: CDS
<222> LOCATION: (54)..(512)

<400> SEQUENCE: 1
gctgctcctc tgtcgagctg atcacaccca cagttgagct gcgctggcca gag atg        56
                                                         Met
                                                         1 cct gcc cac agc ctg gtg atg agc agc ccg gcc ctc ccg gcc ttc ctg    104
Pro Ala His Ser Leu Val Met Ser Ser Pro Ala Leu Pro Ala Phe Leu
        5                  10                 15
```

```
ctc tgc agc acg ctg ctg gtc atc aag atg tac gtg gtg gcc atc atc        152
Leu Cys Ser Thr Leu Leu Val Ile Lys Met Tyr Val Val Ala Ile Ile
        20                  25                  30 acg ggc caa gtg agg ctg cgg aag aag gcc ttt gcc aac ccc gag gat        200
Thr Gly Gln Val Arg Leu Arg Lys Lys Ala Phe Ala Asn Pro Glu Asp
35                  40                  45 gcc ctg aga cac gga ggc ccc cag tat tgc agg agc gac ccc gac gtg        248
Ala Leu Arg His Gly Gly Pro Gln Tyr Cys Arg Ser Asp Pro Asp Val
50                  55                  60                  65 gaa cgc tgc ctc agg gcc cac cgg aac gac atg gag acc atc tac ccc        296
Glu Arg Cys Leu Arg Ala His Arg Asn Asp Met Glu Thr Ile Tyr Pro
                70                  75                  80 ttc ctt ttc ctg ggc ttc gtc tac tcc ttt ctg ggt cct aac cct ttt        344
Phe Leu Phe Leu Gly Phe Val Tyr Ser Phe Leu Gly Pro Asn Pro Phe
            85                  90                  95 gtc gcc tgg atg cac ttc ctg gtc ttc ctc gtg ggc cgt gtg gca cac        392
Val Ala Trp Met His Phe Leu Val Phe Leu Val Gly Arg Val Ala His
            100                 105                 110 acc gtg gcc tac ctg ggg aag ctg cgg gca ccc atc cgc tcc gtg acc        440
Thr Val Ala Tyr Leu Gly Lys Leu Arg Ala Pro Ile Arg Ser Val Thr
    115                 120                 125 tac acc ctg gcc cag ctc ccc tgc gcc tcc atg gct ctg cag atc ctc        488
Tyr Thr Leu Ala Gln Leu Pro Cys Ala Ser Met Ala Leu Gln Ile Leu
130                 135                 140                 145 tgg gaa gcg gcc cgc cac ctg tga ccagcagctg atgcctcctt ggccaccaga      542
Trp Glu Ala Ala Arg His Leu
                150 ccatgggcca agagccgccg tgctatacc tggggacttg atgttccttc cagattgtgg       602 tgggccctga gtcctggttt cctggcagcc tgctgcgcgt gtgggtctct gggcacagtg      662 ggcctgtgtg tgtgcccgtg tgtgtgtatg tgtgtgtgta tgtttcttag ccccttggat      722 tcctgcacga agtggctgat gggaaccatt caagacagat tgtgaagat  tgatagaaaa      782 tccttcagct aaagtaacag agcatcaaaa acatcactcc ctctccctcc ctaacagtga     842 aaagagagaa gggagactct atttaagatt cccaaaccta atgatcatct gaatcccggg      902 ctaagaatgc agacttttca gactgacccc agaaattctg gcccagccaa tctagaggca     962 agcctggcca tctgtatttt ttttttttcca agacagagtc ttgctctgtt gcccaagctg    1022 gagtgaagtg gtacaatctg gctcactgca gcctccgcct cccgggttca gcgattctc     1082 ccgcctcagc ctcctgagta gctgggatta caggcgcgta tcaccatacc cagctaattt    1142 ttgtattttt agtagagacg ggttcaccat gttgcccagg agggtctcga actcctggcc    1202 tcaagtgatc caccggcctc ggcctcccaa agtgctggga tgacaggcat gaatcactgt    1262 gctcagccac catctggagt tttaaaaggc tcccatgtga gtccctgtga tggccaggcc    1322 aggggaccccc tgccagttct ctgtggaagc aaggctgggg tcttgggttc ctgtatggtg  1382 gaagctgggt gagccaagga cagggctggc tcctctgccc ccgctgacgc ttcccttgcc   1442 gttggctttg gatgtctttg ctgcagtctt ctctctggct caggtgtggg tgggaggggc    1502 ccacaggaag ctcagccttc tcctcccaag gtttgagtcc ctccaaaggg cagtgggtgg   1562 aggaccggga gctttgggtg accagccact caaaggaact ttctggtccc ttcagtatct    1622 tcaaggttg gaaactgcaa atgtcccctt gatggggaat ccgtgtgtgt gtgtgtgtgt    1682 gtgtgtgtgt gtgtgtgtgt gtgtgttttc tcctagaccc gtgacctgag atgtgtgatt    1742 tttagtcatt aaatggaagt gtctgccagc tgggcccagc acctaaaaaa aaaaaaaaa   1802 aaa                                                                1805
```

<210> SEQ ID NO 2
<211> LENGTH: 152
<212> TYPE: PRT
<213> ORGANISM: Homo sapiens

<400> SEQUENCE: 2

Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
            20                  25                  30

Ile Thr Gly Gln Val Arg Leu Arg Lys Lys Ala Phe Ala Asn Pro Glu
        35                  40                  45

Asp Ala Leu Arg His Gly Gly Pro Gln Tyr Cys Arg Ser Asp Pro Asp
    50                  55                  60

Val Glu Arg Cys Leu Arg Ala His Arg Asn Asp Met Glu Thr Ile Tyr
65                  70                  75                  80

Pro Phe Leu Phe Leu Gly Phe Val Tyr Ser Phe Leu Gly Pro Asn Pro
                85                  90                  95

Phe Val Ala Trp Met His Phe Leu Val Phe Leu Val Gly Arg Val Ala
            100                 105                 110

His Thr Val Ala Tyr Leu Gly Lys Leu Arg Ala Pro Ile Arg Ser Val
        115                 120                 125

Thr Tyr Thr Leu Ala Gln Leu Pro Cys Ala Ser Met Ala Leu Gln Ile
    130                 135                 140

Leu Trp Glu Ala Ala Arg His Leu
145                 150

<210> SEQ ID NO 3
<211> LENGTH: 3651
<212> TYPE: DNA
<213> ORGANISM: Mus musculus
<220> FEATURE:
<221> NAME/KEY: CDS
<222> LOCATION: (80)..(541)

<400> SEQUENCE: 3
ctctccataa gccgcctgtg ggacagtctc actctcagtc ccggtgtccc cgagttgaag      60
tccaggccgg ctagccgag atg cct tcc ccg ggc ctg gtg atg gag agc ggc     112
                    Met Pro Ser Pro Gly Leu Val Met Glu Ser Gly
                    1               5                   10 cag gtg ctc ccg gcc ttt ctg ctc tgc agc aca ctg ctg gtc atc aag     160
Gln Val Leu Pro Ala Phe Leu Leu Cys Ser Thr Leu Leu Val Ile Lys
            15                  20                  25 atg tac gcg gtg gct gtc atc aca ggc cag atg agg ctg cgg aag aag     208
Met Tyr Ala Val Ala Val Ile Thr Gly Gln Met Arg Leu Arg Lys Lys
        30                  35                  40 gct ttt gcc aac ccc gag gat gcg ctg aaa cgt gga ggc ctc cag tat     256
Ala Phe Ala Asn Pro Glu Asp Ala Leu Lys Arg Gly Gly Leu Gln Tyr
    45                  50                  55 tac agg agt gac cca gat gtg gag cgc tgc ctc aga gcc cac cgc aac     304
Tyr Arg Ser Asp Pro Asp Val Glu Arg Cys Leu Arg Ala His Arg Asn
60                  65                  70                  75 gac atg gag aca atc tat cct ttc ctc ttc ctc ggc ttc gtg tac tca     352
Asp Met Glu Thr Ile Tyr Pro Phe Leu Phe Leu Gly Phe Val Tyr Ser
                80                  85                  90 ttc ctg gga ccc aac cct ctg atc gcc tgg ata cat ttc ctc gtt gtc     400
Phe Leu Gly Pro Asn Pro Leu Ile Ala Trp Ile His Phe Leu Val Val
            95                  100                 105

```
ctc aca ggc cgt gtg gta cac acc gtg gcc tac ctg ggc aag ctg aac        448
Leu Thr Gly Arg Val Val His Thr Val Ala Tyr Leu Gly Lys Leu Asn
        110                 115                 120 cca cgc ctt cgc tcc ggg gcc tat gtc ctg gcc cag ttc tcc tgt ttc        496
Pro Arg Leu Arg Ser Gly Ala Tyr Val Leu Ala Gln Phe Ser Cys Phe
    125                 130                 135 tcc atg gcc ctg cag atc ctc tgg gag gtg gcc cac cat ctg tga            541
Ser Met Ala Leu Gln Ile Leu Trp Glu Val Ala His His Leu
140                 145                 150 ccagcagctg aagcctcctc agctaccaca gtggggacag agccatgaag gctgaacttg      601
cggacttggt gtctcttcta gaatagggac ggggtctggt cctggggtcc tgggtaacct      661
gggcgagtgg atctcagggc ccaatgtgca catgtgtgtt tcttagcctt ttgggatgct      721
agatgaagtc ccatttggag ccacttacag atgagctgtc aagatttgag aggacatcct      781
tcacctcaca aaatgcctta acatcacac cacactccct cttaaccata aaataaagga       841
caggattgac caacagagcc atcatcccat ataggactaa gaatgaaggc ttctcagacc      901
tacctacaat tctggcccag cccaaggaga gccacctggc tggtatgtgt ccgaggacat      961
cctcacaaga ggcccagcag tggccagctc atgtggagg tagagtgctt gctattttta      1021
gaggtgggca ggtcagagca tccctgtccc ctgttgatac caccgtcctt tgagtgcctt     1081
aggtagcaca ggctcagggg ggtgagaatg tccacagctc agcctccttg tgcatggctt     1141
tggctcctcc aaagacggaa aggatgggct ttgaccaacc cctggaaggg aactttggct     1201
tcttcagcat ctgtgaggtt tgaagatgcc aaatgtctac tcctgtggaa aatctcactt     1261
gtgtgtgtgc agtgtccctc cagagtcctg agacctgttt aggtttagtc attaaacagc     1321
agagtgtgac ctgtgaatgt tcggtgtcta agacccatgc tgtgccagcc ggcctggtac     1381
ctatgggagt tttcacgttc cggtgtgtgt atgttttact tttatgagac aaggtctcac     1441
ttagcccgag ttggcctcaa acttactcta cagtcaggac aaccttgagc tgacagccta    1501
cctgtgcctc ctaagtgctg ggatcgccgg cctgcaccac catagtgcca agccagtaca    1561
ggcaacttcc accaggctgc tccagagaag tccctgacaa gatggtgttt ggcttgggat    1621
ccagagatgt ccaaatcctg tcttccacgt ggcgattctt tctgcagctc tgccaccttg    1681
tagggtgctg gttttctgct ctacagacgg agacggaagt gactacctga aggaaggcat    1741
agggtgtgct ccagaacctg ggacattcag gctcccaggc ttcccacaca agcctagcca    1801
caccacttct cctcccagcg gggcaagccc tgtgccccag acctgctcta tggggttggg    1861
gagggggttt tactggaaag ccctgctggc ctaggcttca gcctcacaca gctggtgttc    1921
tgggagtgaa tagcactgcc ctctggtggt gagttgaaac ctttgctctt ggaatgctca    1981
tctgagaaaa caaaaactgt agaatggggc cctcttgaa tgccagctgt cgctgaacat     2041
taggctggat gcgaccttca tctgtcattg tcaccccaac cccaatgccc cagttaatac    2101
ttaaatttta gataagacca ggtgaattca gacaaaagcc ttttttcctg cgttttaatt    2161
ttctgtggat gggtgttttg tatgaatgtc tgtctgtatc ataggtgtac ctggtgccca    2221
tggagaccag aagaagttgc tggagctgga gttagacaca ttgtgagcca tcatgtggat    2281
actgggaatt gaacccgggt tctctgaaga gcaaccagtg ctcttaacca ctgagccatt    2341
tctccagacc cattttaga taagggattc aaggatccaa gaagacttgt cctgaattcc     2401
tgagctagca tagtcaaaaa ctttgcaaga tgggacccag gagagagagg actggagagt    2461
ccatgcaggg cgtataaata tcatctact tcagtctttt cctctcagga aggtgagatt     2521
gtgagggcca ggtgtaagaa cctgccagtt gcctgatgca gaccatgcat tgcccacaag    2581
```

```
gtctgcctgc tgtggggcct gcgagatgga ggccagggcc cctcggaggg tctactcatt    2641
tgtctttctt gcccatcccc tggcactgca gtgggaaagg caccaagcaa gggacagtga    2701
cagcctcatg tggggtaaga aggctcagtc tctgatccc tgctgggcag ggaggtgagt     2761
tacgctaatg ctggccagga tgtataaaga aattcaagtg tgcacacctt caatccagca    2821
cacaggcagg tggatagctg agttggaagc cagcgtggtc tacccagtga gtccttgtct    2881
caaaagcaaa gaaatcagta cctgtgtgcc atggtatgaa gttgaaattg gagggtggg    2941 aaatcggggt aagagggcca ttaaggaggc cgaggtaccc tttctatgtt ccaagcagga    3001
gagaggtggg gacagtggtt tcagcagggt gtcactgggc agttggcagg agcagagaca    3061
ggacctagtg gcttgttctg atccagccct catgataggg aatacaggga gtgatctcct    3121
ggctgcaaat ctggactcaa gacaggtggc tccaggccac agcacagagc aaagcactgt    3181
ccagggaggc agtgtggctg gtgccacctg ccaatccagc cagaggctgc aacacagcac    3241
ctgcagccct caagccctgc taccacagca gcatctcttg catctctcga ttcctttttt    3301
tttctgacat ggtctcttgt ctgaggccat tgtggtggc ttgaatagga atggcccccc     3361
aataaactca tgtgtttgac tgcttagccc atagggagga gtggcattat taagaggtgt    3421
ggccttgttg gaggtggtgt gtcactgtga ggtgggcttt ggggtctcat atgctcaatc    3481
tcagcctact ggggcagtcc cctgctgcct tcagatcaag ttgtagaact ctgatctcct    3541
tctccagcac catgtctgcc ttcatgccat gttcccacca tgatgataaa ggactaaacc    3601
tctgaacctg taagtcagcc ccaattaaat gctttccttt ataagaaaaa               3651
```

<210> SEQ ID NO 4
<211> LENGTH: 153
<212> TYPE: PRT
<213> ORGANISM: Mus musculus

<400> SEQUENCE: 4

```
Met Pro Ser Pro Gly Leu Val Met Glu Ser Gly Gln Val Leu Pro Ala
1               5                   10                  15

Phe Leu Leu Cys Ser Thr Leu Leu Val Ile Lys Met Tyr Ala Val Ala
            20                  25                  30

Val Ile Thr Gly Gln Met Arg Leu Arg Lys Lys Ala Phe Ala Asn Pro
        35                  40                  45

Glu Asp Ala Leu Lys Arg Gly Gly Leu Gln Tyr Tyr Arg Ser Asp Pro
    50                  55                  60

Asp Val Glu Arg Cys Leu Arg Ala His Arg Asn Asp Met Glu Thr Ile
65                  70                  75                  80

Tyr Pro Phe Leu Phe Leu Gly Phe Val Tyr Ser Phe Leu Gly Pro Asn
                85                  90                  95

Pro Leu Ile Ala Trp Ile His Phe Leu Val Val Leu Thr Gly Arg Val
            100                 105                 110

Val His Thr Val Ala Tyr Leu Gly Lys Leu Asn Pro Arg Leu Arg Ser
        115                 120                 125

Gly Ala Tyr Val Leu Ala Gln Phe Ser Cys Phe Ser Met Ala Leu Gln
    130                 135                 140

Ile Leu Trp Glu Val Ala His His Leu
145                 150
```

<210> SEQ ID NO 5
<211> LENGTH: 1257
<212> TYPE: DNA
<213> ORGANISM: Rattus norvegicus

```
<220> FEATURE:
<221> NAME/KEY: CDS
<222> LOCATION: (43)..(504)

<400> SEQUENCE: 5
ccctcagtcc cggtgtcccg gagtccaggc tggctagctg ag atg act tcc ctg         54
                                              Met Thr Ser Leu
                                                1 ggt ttg gtg atg gag aac agc cag gtg ctc ccc gcc ttt ctg ctc tgc       102
Gly Leu Val Met Glu Asn Ser Gln Val Leu Pro Ala Phe Leu Leu Cys
  5              10                  15                  20 agc aca ctg ctg gtc atc aag atg tac gcg gtg gct gtc atc aca ggc       150
Ser Thr Leu Leu Val Ile Lys Met Tyr Ala Val Ala Val Ile Thr Gly
             25                  30                  35 caa gtc agg ctg cgg aag aag gct ttt gcc aac ccc gag gac gcg ttg       198
Gln Val Arg Leu Arg Lys Lys Ala Phe Ala Asn Pro Glu Asp Ala Leu
         40                  45                  50 aaa cgt gga ggt ctc cag tac tgc agg agt gac cca gat gtg gag cgc       246
Lys Arg Gly Gly Leu Gln Tyr Cys Arg Ser Asp Pro Asp Val Glu Arg
     55                  60                  65 tgc ctc aga gcc cac cgc aac gac atg gag acg atc tac ccc ttc ctc       294
Cys Leu Arg Ala His Arg Asn Asp Met Glu Thr Ile Tyr Pro Phe Leu
 70                  75                  80 ttc ctt ggt ttc gtc tac tca ttc ctg gga ccc aac cct ctc atc gcc       342
Phe Leu Gly Phe Val Tyr Ser Phe Leu Gly Pro Asn Pro Leu Ile Ala
 85                  90                  95                 100 tgg ata cat ttc ctc gtg gtc ctc aca ggc cgt gtg gta cac acc gtg       390
Trp Ile His Phe Leu Val Val Leu Thr Gly Arg Val Val His Thr Val
                105                 110                 115 gcc tac ctg ggc aaa atg aac cca cgc att cgc tcc ggg gcc tat gtt       438
Ala Tyr Leu Gly Lys Met Asn Pro Arg Ile Arg Ser Gly Ala Tyr Val
            120                 125                 130 ctg gcc cag ttc gcc tgt ttc tcc atg gcc cta cag atc ctc tgg gaa       486
Leu Ala Gln Phe Ala Cys Phe Ser Met Ala Leu Gln Ile Leu Trp Glu
        135                 140                 145 gtg gcc cac cat ctg tga ccagcagctg aagcctcctc agataccaca              534
Val Ala His His Leu
            150 atgggagacg gagccatgaa ggctgaacca gaggacttgg tgccccttct agaacaggga     594 tgggctcagg tccagggttc ctggctaagc taggtgtgtg gatctctgag cctaatgtgc     654 aaatgtgtgt cttagccttt tgggaccctg ggtgatgtgt ccgattagaa ccgcttacag     714 attgacagaa catccttcac ctcacaaatg ccttaaactt cctcttaccc ataaagcaaa     774 ggacagaaga ttgtccaaca gagccatcat gccatatagg gctaaggatg agggcttctc     834 agacctacct gtaattctgg cacagccaga ggagagacac gtgactggtg tgtgtctcag     894 ggcgtcctca caagagggcc agcagtggcc ggctcccagt ggaagtaggg tgccatgttt     954 tcagaggagg gcaggtcaga gcttccctgt ccctgttga tacctctctg tcctgcctta    1014 gctagcacag gctcagggtg aagcaaatgt tcccagctca gcctgctcct gcgcggcctt    1074 ggctcctcca aagactgaaa gtcaaggatg gctttgacc aaccgctaaa aaccgcacct     1134 gtgaggtttg aagatgccaa acatctactc ctgtgaaaaa tctcacctat gtgtgtgcag    1194 tgtccctcca gagtcctcct gagaccggtt caggcttagc cattaaacag cagagtgtga    1254 ccg                                                                 1257
```

<210> SEQ ID NO 6
<211> LENGTH: 153
<212> TYPE: PRT
<213> ORGANISM: Rattus norvegicus

<400> SEQUENCE: 6

```
Met Thr Ser Leu Gly Leu Val Met Glu Asn Ser Gln Val Leu Pro Ala
1               5                   10                  15

Phe Leu Leu Cys Ser Thr Leu Leu Val Ile Lys Met Tyr Ala Val Ala
            20                  25                  30

Val Ile Thr Gly Gln Val Arg Leu Arg Lys Lys Ala Phe Ala Asn Pro
        35                  40                  45

Glu Asp Ala Leu Lys Arg Gly Gly Leu Gln Tyr Cys Arg Ser Asp Pro
    50                  55                  60

Asp Val Glu Arg Cys Leu Arg Ala His Arg Asn Asp Met Glu Thr Ile
65                  70                  75                  80

Tyr Pro Phe Leu Phe Leu Gly Phe Val Tyr Ser Phe Leu Gly Pro Asn
                85                  90                  95

Pro Leu Ile Ala Trp Ile His Phe Leu Val Val Leu Thr Gly Arg Val
            100                 105                 110

Val His Thr Val Ala Tyr Leu Gly Lys Met Asn Pro Arg Ile Arg Ser
        115                 120                 125

Gly Ala Tyr Val Leu Ala Gln Phe Ala Cys Phe Ser Met Ala Leu Gln
    130                 135                 140

Ile Leu Trp Glu Val Ala His His Leu
145                 150
```

<210> SEQ ID NO 7
<211> LENGTH: 876
<212> TYPE: DNA
<213> ORGANISM: Bos Taurus
<220> FEATURE:
<221> NAME/KEY: CDS
<222> LOCATION: (9)..(470)

<400> SEQUENCE: 7

```
ccaccgag atg ccg ccc tcc ggc ctg gag ctg atg aac ggc cag gtg ctc        50
         Met Pro Pro Ser Gly Leu Glu Leu Met Asn Gly Gln Val Leu
         1               5                   10 ccc gcc ttc ctg ctc tgc agc gcg ctg ctg gtc atc aaa atg tac gtg        98
Pro Ala Phe Leu Leu Cys Ser Ala Leu Leu Val Ile Lys Met Tyr Val
15                  20                  25                  30 gtg gcc gtc atc acc ggc caa gtg agg ctg cgg aag aag gct ttt gcc       146
Val Ala Val Ile Thr Gly Gln Val Arg Leu Arg Lys Lys Ala Phe Ala
                35                  40                  45 aac ccc gag gac gct cag aga cat gga ggc ctc cag tat tgc cgg aac       194
Asn Pro Glu Asp Ala Gln Arg His Gly Gly Leu Gln Tyr Cys Arg Asn
            50                  55                  60 gac cca gat gtg gaa cgc tgc ctc aga gcc cac cgg aat gac atg gag       242
Asp Pro Asp Val Glu Arg Cys Leu Arg Ala His Arg Asn Asp Met Glu
        65                  70                  75 acc atc tac ccc ttc ctg ttc ctg ggc ttt gtc tac tct ttc ctc gga       290
Thr Ile Tyr Pro Phe Leu Phe Leu Gly Phe Val Tyr Ser Phe Leu Gly
    80                  85                  90 ccg aac ccc ttc gtc gcc cgg atg cac ttc ctg gtc ttc ttc ctg ggc       338
Pro Asn Pro Phe Val Ala Arg Met His Phe Leu Val Phe Phe Leu Gly
95                  100                 105                 110 cgt atg gta cac acc gtg gca tac ctg ggg aaa ctg cgg gcg ccc acc       386
Arg Met Val His Thr Val Ala Tyr Leu Gly Lys Leu Arg Ala Pro Thr
                115                 120                 125
```

| | |
|---|---|
| cgc tcc ctg gcc tac acc ctg gcc cag ctc ccc tgc gcc tcc atg gcc<br>Arg Ser Leu Ala Tyr Thr Leu Ala Gln Leu Pro Cys Ala Ser Met Ala<br>            130                   135                  140 | 434 |
| ctg cag att gtc tgg gag gca gcc cgc cac ctg tga ccagccgtgg<br>Leu Gln Ile Val Trp Glu Ala Ala Arg His Leu<br>            145                   150 | 480 |
| acgccacctc ggccgccaga ccgctggcca cgagccagcg ggctgaacc tggggaccg | 540 |
| atggcccttt gagattgtga caggccctgg ggctgggttc ctggcaactg ctgagcacg | 600 |
| tgatcttggg cccaggggc ctgtgtgtgt tccccgtgt gtcccttgga ttcctgggtg | 660 |
| aagcggctga tttggaactg tttagagacg gaccgtcacg attgatagaa aattcttcca | 720 |
| ctgtaaaaaa ctctctccct ccctccctcc ctcctcctcc ccaatgctgg aaaagcaaa | 780 |
| cagagactca gttctggttt tggaacataa cgaccttctg aatccaggga tgtaataaat | 840 |
| gaggacttct cacctacaaa aaaaaaaaaa aaaaaa | 876 |

<210> SEQ ID NO 8
<211> LENGTH: 153
<212> TYPE: PRT
<213> ORGANISM: Bos Taurus

<400> SEQUENCE: 8

```
Met Pro Pro Ser Gly Leu Glu Leu Met Asn Gly Gln Val Leu Pro Ala
1               5                   10                  15

Phe Leu Leu Cys Ser Ala Leu Leu Val Ile Lys Met Tyr Val Val Ala
            20                  25                  30

Val Ile Thr Gly Gln Val Arg Leu Arg Lys Lys Ala Phe Ala Asn Pro
        35                  40                  45

Glu Asp Ala Gln Arg His Gly Gly Leu Gln Tyr Cys Arg Asn Asp Pro
    50                  55                  60

Asp Val Glu Arg Cys Leu Arg Ala His Arg Asn Asp Met Glu Thr Ile
65                  70                  75                  80

Tyr Pro Phe Leu Phe Leu Gly Phe Val Tyr Ser Phe Leu Gly Pro Asn
                85                  90                  95

Pro Phe Val Ala Arg Met His Phe Leu Val Phe Phe Leu Gly Arg Met
            100                 105                 110

Val His Thr Val Ala Tyr Leu Gly Lys Leu Arg Ala Pro Thr Arg Ser
        115                 120                 125

Leu Ala Tyr Thr Leu Ala Gln Leu Pro Cys Ala Ser Met Ala Leu Gln
    130                 135                 140

Ile Val Trp Glu Ala Ala Arg His Leu
145                 150
```

<210> SEQ ID NO 9
<211> LENGTH: 1447
<212> TYPE: DNA
<213> ORGANISM: Equus caballus
<220> FEATURE:
<221> NAME/KEY: CDS
<222> LOCATION: (27)..(488)

<400> SEQUENCE: 9

| | |
|---|---|
| gcacgagcgg agctcctgcc gccgag atg cca ccc cct agc ctc gcg atg gtg<br>                                             Met Pro Pro Pro Ser Leu Ala Met Val<br>                                             1                   5 | 53 |
| agt ggc cag gcg ctc ccg gcc ttc ctg ctc tgc agc acg ctg ctg gtc<br>Ser Gly Gln Ala Leu Pro Ala Phe Leu Leu Cys Ser Thr Leu Leu Val<br> 10                  15                   20                   25 | 101 |

```
atc aag atg tac gcg gtg gcc gtc atc acg ggc caa gtg agg ctg agg    149
Ile Lys Met Tyr Ala Val Ala Val Ile Thr Gly Gln Val Arg Leu Arg
            30                  35                  40 aag aag gct ttc gcc aac ccc gag gac gcc ctg aga cac gga ggc ctc    197
Lys Lys Ala Phe Ala Asn Pro Glu Asp Ala Leu Arg His Gly Gly Leu
        45                  50                  55 cag ttt cac cgg gac gac cag gac gtg gag cgt tgc ctg aga gcc cac    245
Gln Phe His Arg Asp Asp Gln Asp Val Glu Arg Cys Leu Arg Ala His
        60                  65                  70 cgg aac gac atg gag acc atc tac ccc ttc ctg ttc ctg ggc ctc gtc    293
Arg Asn Asp Met Glu Thr Ile Tyr Pro Phe Leu Phe Leu Gly Leu Val
75                  80                  85 tac tcc ttc ctg ggg ccc gac cct ttc gtg gcc cag atg cac ttt ctc    341
Tyr Ser Phe Leu Gly Pro Asp Pro Phe Val Ala Gln Met His Phe Leu
90                  95                 100                 105 gtc ttc ttc ctg ggc cgc atg gtg cac acc gtg gcc tac ctg ggg aag    389
Val Phe Phe Leu Gly Arg Met Val His Thr Val Ala Tyr Leu Gly Lys
            110                 115                 120 ctg cgg gcg ccc acc cgc tct ctg gcc tac acc gtg gcc cag ctc ccc    437
Leu Arg Ala Pro Thr Arg Ser Leu Ala Tyr Thr Val Ala Gln Leu Pro
            125                 130                 135 tgc gcc tcg atg gcc ctg cag atc gtc tgg gaa gca gcc cgc cac ctg    485
Cys Ala Ser Met Ala Leu Gln Ile Val Trp Glu Ala Ala Arg His Leu
            140                 145                 150 tga ccgccagctg agacctcctt gccgccagac cgctgaccgt gagccgccta         538
ggggattggg catcccttcc agattgtgac aggccctggg gcctggtttc ctggcaaact   598
gctgagcgcg ggatcctgga cccagtgcac ctgtgtgtgt ttgcatatgt gtgtgtttgc   658
acatgtgcgt gtgtgcgccc cttggattcc tgggtgaagt ggccgatgga gcccgtttag   718
agacgagctg tcaagattga tagaaaaccc ttccactcaa ataatagagc atttaaataa   778
tagagcattt aaaacatgac tccttcttca tcatccctaa gagcaggaag agtgagragg   838
gccagttcag attcctgagc ctaatggtca tcggatccag ggctgtagta aatgcagact   898
tctcagaccc accccagaaa ttctggttca gcctatttag aggggggcct gggcatctgc   958
attttttgta aagctcctgg tgagtcccag cacgggcggg tcccgagccc ctggcagccc  1018
cctctagagg cagggccagg acgcgcaggg tgtgttgcga tttcttttac ggccggagtt  1078
cagtgagggg gcattatgct cggtgccctc cggtcagtcc acatccctca ctggagcctt  1138
ctctgcctgg caccggggcg gatgggaggg gccccggtg acgtctgcct tctctccctg    1198
aggtttctgt cgctcctgaa ggctgtaaat caaggacaat gggccttgaa ggaccaaccg  1258
caaaagggaa cttactggct ccttcagtat ctgcaggatt tgaaaaccgc aaatgtgcct  1318
cctgtgagaa atgtgtgtgt gtgtgcgtgt gtgcatgtgg aatccacgtg tctctcctag  1378
actcctgttc tgagacgtgt gtggctttaa tcattaaatg gagcctttgg caaaaaaaaa  1438
aaaaaaaaa                                                         1447

<210> SEQ ID NO 10
<211> LENGTH: 153
<212> TYPE: PRT
<213> ORGANISM: Equus caballus

<400> SEQUENCE: 10

Met Pro Pro Pro Ser Leu Ala Met Val Ser Gly Gln Ala Leu Pro Ala
1               5                   10                  15

Phe Leu Leu Cys Ser Thr Leu Leu Val Ile Lys Met Tyr Ala Val Ala
            20                  25                  30
```

```
Val Ile Thr Gly Gln Val Arg Leu Arg Lys Lys Ala Phe Ala Asn Pro
         35                  40                  45

Glu Asp Ala Leu Arg His Gly Gly Leu Gln Phe His Arg Asp Asp Gln
 50                  55                  60

Asp Val Glu Arg Cys Leu Arg Ala His Arg Asn Asp Met Glu Thr Ile
 65                  70                  75                  80

Tyr Pro Phe Leu Phe Leu Gly Leu Val Tyr Ser Phe Leu Gly Pro Asp
                 85                  90                  95

Pro Phe Val Ala Gln Met His Phe Leu Val Phe Leu Gly Arg Met
                100                 105                 110

Val His Thr Val Ala Tyr Leu Gly Lys Leu Arg Ala Pro Thr Arg Ser
                115                 120                 125

Leu Ala Tyr Thr Val Ala Gln Leu Pro Cys Ala Ser Met Ala Leu Gln
                130                 135                 140

Ile Val Trp Glu Ala Ala Arg His Leu
145                 150
```

<210> SEQ ID NO 11
<211> LENGTH: 446
<212> TYPE: DNA
<213> ORGANISM: Danio rerio
<220> FEATURE:
<221> NAME/KEY: CDS
<222> LOCATION: (1)..(441)

<400> SEQUENCE: 11

```
atg ctc ggg agc gac ata cag ttg tgc ttc atc ttc tac agc acg ctt    48
Met Leu Gly Ser Asp Ile Gln Leu Cys Phe Ile Phe Tyr Ser Thr Leu
 1               5                  10                  15 tta atc ttg aag atg tac att att gcc atc atc aca ggc caa gtg aga    96
Leu Ile Leu Lys Met Tyr Ile Ile Ala Ile Ile Thr Gly Gln Val Arg
                20                  25                  30 ctt cgg aaa aag gcg ttt gct aac cca gag gac gcc gag aga cac gga   144
Leu Arg Lys Lys Ala Phe Ala Asn Pro Glu Asp Ala Glu Arg His Gly
             35                  40                  45 ggt gtg cag ttc tgc cgc acg gat cca tat gtg gag cgc tgt agg aga   192
Gly Val Gln Phe Cys Arg Thr Asp Pro Tyr Val Glu Arg Cys Arg Arg
 50                  55                  60 gca cag cag aat gac atg gag aac att ttg ccc ttt tta ttt ctt gga   240
Ala Gln Gln Asn Asp Met Glu Asn Ile Leu Pro Phe Leu Phe Leu Gly
 65                  70                  75                  80 gcg gtc tac tcc atg aca agc cca tca tat gca gca gca caa ctt cat   288
Ala Val Tyr Ser Met Thr Ser Pro Ser Tyr Ala Ala Ala Gln Leu His
                 85                  90                  95 ttc ctc atc ttc ttc ctg ggt cga gtt ctt cac agc gtt gca tat ctg   336
Phe Leu Ile Phe Phe Leu Gly Arg Val Leu His Ser Val Ala Tyr Leu
                100                 105                 110 ctg gca cta aaa gca ccg aca cgt tca ttg gcc tat gtc atc gct cag   384
Leu Ala Leu Lys Ala Pro Thr Arg Ser Leu Ala Tyr Val Ile Ala Gln
                115                 120                 125 gtg cct tgc att tca atg gcc ata cag ata ctc atg gaa gtg gcc tca   432
Val Pro Cys Ile Ser Met Ala Ile Gln Ile Leu Met Glu Val Ala Ser
130                 135                 140 ttc gca tga aaaaa                                                  446
Phe Ala
145
```

```
-continued

<210> SEQ ID NO 12
<211> LENGTH: 146
<212> TYPE: PRT
<213> ORGANISM: Danio rerio

<400> SEQUENCE: 12

Met Leu Gly Ser Asp Ile Gln Leu Cys Phe Ile Phe Tyr Ser Thr Leu
1               5                   10                  15

Leu Ile Leu Lys Met Tyr Ile Ile Ala Ile Ile Thr Gly Gln Val Arg
            20                  25                  30

Leu Arg Lys Lys Ala Phe Ala Asn Pro Glu Asp Ala Glu Arg His Gly
        35                  40                  45

Gly Val Gln Phe Cys Arg Thr Asp Pro Tyr Val Glu Arg Cys Arg Arg
    50                  55                  60

Ala Gln Gln Asn Asp Met Glu Asn Ile Leu Pro Phe Leu Phe Leu Gly
65                  70                  75                  80

Ala Val Tyr Ser Met Thr Ser Pro Ser Tyr Ala Ala Ala Gln Leu His
                85                  90                  95

Phe Leu Ile Phe Phe Leu Gly Arg Val Leu His Ser Val Ala Tyr Leu
                100                 105                 110

Leu Ala Leu Lys Ala Pro Thr Arg Ser Leu Ala Tyr Val Ile Ala Gln
            115                 120                 125

Val Pro Cys Ile Ser Met Ala Ile Gln Ile Leu Met Glu Val Ala Ser
        130                 135                 140

Phe Ala
145
```